(12) United States Patent
Sheta

(10) Patent No.: US 8,920,286 B2
(45) Date of Patent: Dec. 30, 2014

(54) EXERCISE CELL, KETOSIS/WEIGHT LOSS INDUCING EXERCISE MACHINE (KWIEM) KETOSIS INDUCING APPARATUS (KIA)

(71) Applicant: Mostafa Sheta, Henderson, NV (US)

(72) Inventor: Mostafa Sheta, Henderson, NV (US)

(*) Notice: Subject to any disclaimer, the term of this patent is extended or adjusted under 35 U.S.C. 154(b) by 0 days.

(21) Appl. No.: 14/205,752

(22) Filed: Mar. 12, 2014

(65) Prior Publication Data

US 2014/0274563 A1    Sep. 18, 2014

Related U.S. Application Data

(60) Provisional application No. 61/789,800, filed on Mar. 15, 2013.

(51) Int. Cl.
*A63B 24/00* (2006.01)

(52) U.S. Cl.
USPC .................................. 482/2; 482/1; 482/148

(58) Field of Classification Search
USPC ............. 482/1–9, 35, 148, 900–902; 472/136
See application file for complete search history.

(56) References Cited

U.S. PATENT DOCUMENTS

| | | |
|---|---|---|
| 5,342,244 A | 8/1994 | Nelson |
| 5,352,166 A | 10/1994 | Chang |
| 5,799,652 A * | 9/1998 | Kotliar ................ 128/205.11 |
| 6,443,849 B1 | 9/2002 | Byrd |
| 6,740,017 B2 * | 5/2004 | Pino .............................. 482/148 |
| 7,465,257 B1 * | 12/2008 | Morgan, Jr. ..................... 482/57 |
| 7,749,089 B1 * | 7/2010 | Briggs et al. ................. 472/136 |
| 2008/0110115 A1 | 5/2008 | French |
| 2010/0042555 A1 | 2/2010 | Ranen et al. |
| 2011/0004993 A1 | 1/2011 | Frei |
| 2011/0164044 A1 | 7/2011 | Huang |
| 2012/0309551 A1 | 12/2012 | Holzhacker |

\* cited by examiner

*Primary Examiner* — Glenn Richman
(74) *Attorney, Agent, or Firm* — Ronald C. Gorsche

(57) ABSTRACT

A unique concept of exercise and weight loss that takes place in a new invention utility, namely the exercise cells or the Ketone Inducing Apparatus is disclosed. The apparatus consists of four exercise cells to simulate four different exercise categories in extreme environments, namely walk/run/hike in a cold mountain environment, swim/water jogging in a cold water marine environment, cycling in a hot, humid, rainy, tropical forest environment, and gravitational rotation in a hot dry air windy space or desert environment. The purpose of this activity is to maximally stimulate the process of Ketosis (breakage of the human fat) to form smaller molecules of Ketones. The Ketones will then be eliminated both passively from the human body via urination and exhalation and actively through intracellular burn oxidation, hence reducing the extra fat load and reducing obesity. The reduction of the human obesity will enhance the human health status and reduce the complication of obesity namely diabetes, heart disease, and reduce the human mortality and morbidity.

18 Claims, 30 Drawing Sheets

FIG 2A: Front Right Perspective View of the Quadrex
FIG 3A: Front Left Perspective View of the Quadrex.

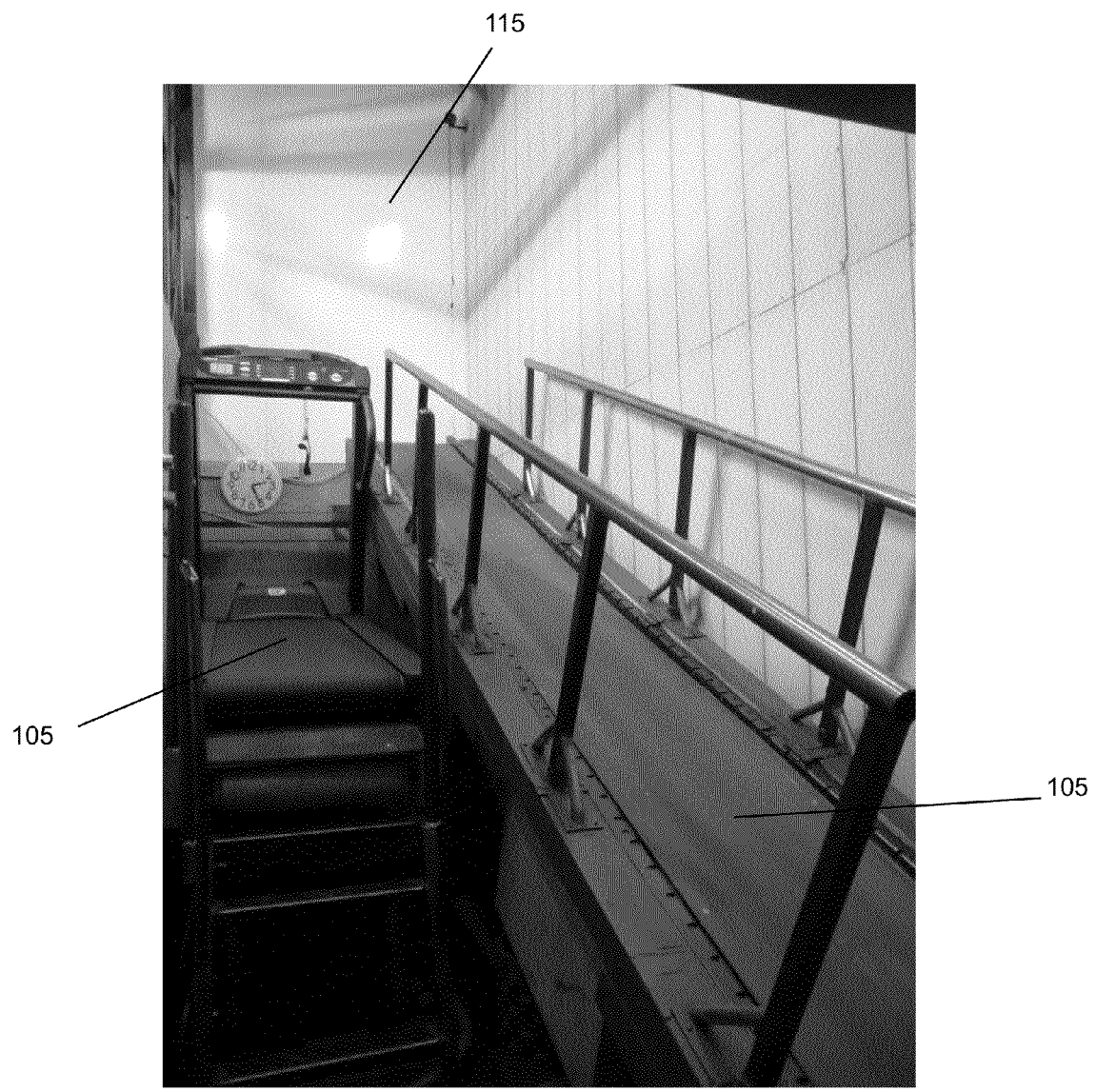
FIG 6B: Conveyor Belt, Treadmill and Projector Screen in the Mountain Cell

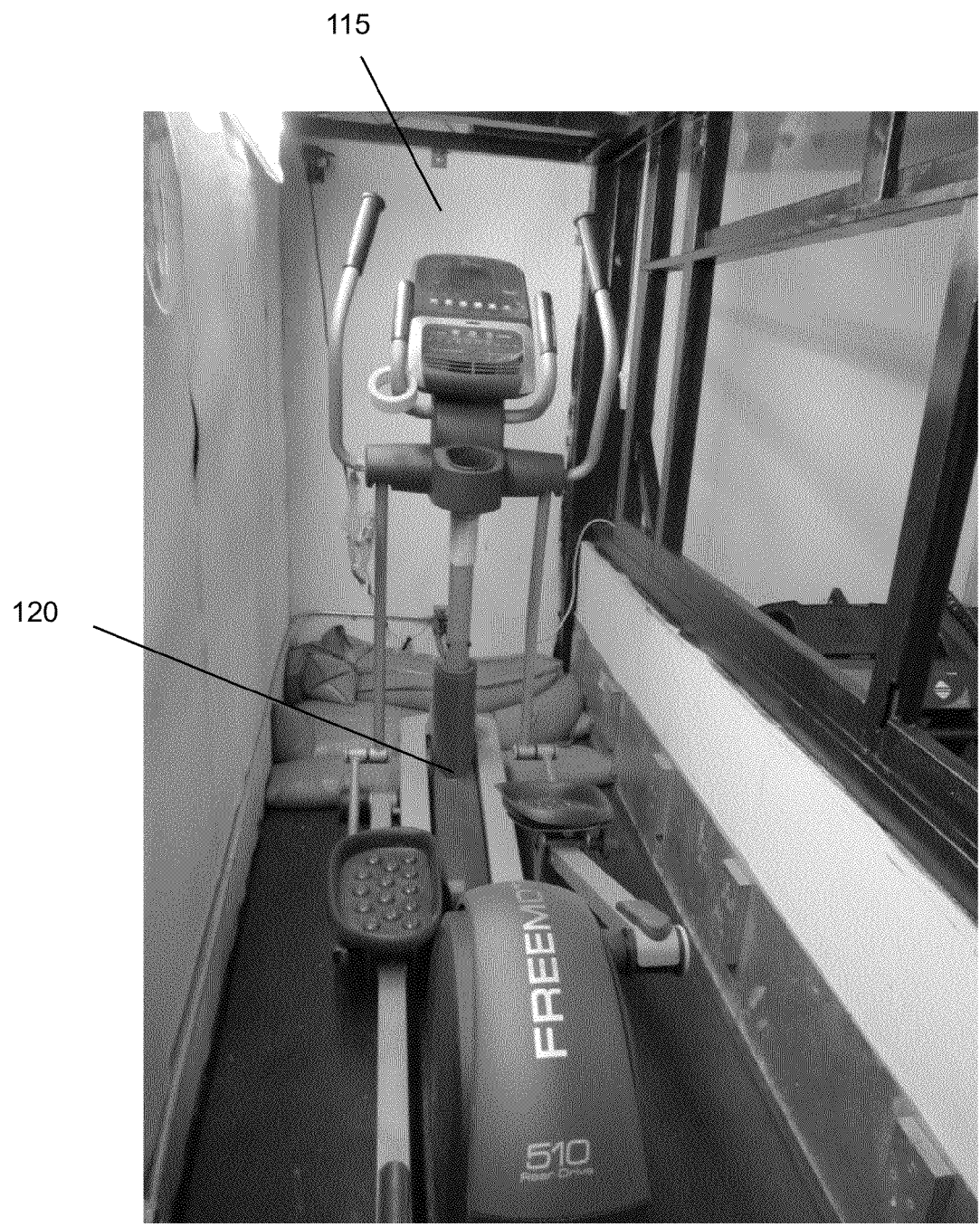
FIG 6C: Elliptical Machine and Projected Screen in the Mountain Cell

FIG. 6D: Subjects on Conveyor Belt and Treadmill

FIG 6E: Subject on the elliptical while watching projection on Screen in the Mountain Cell

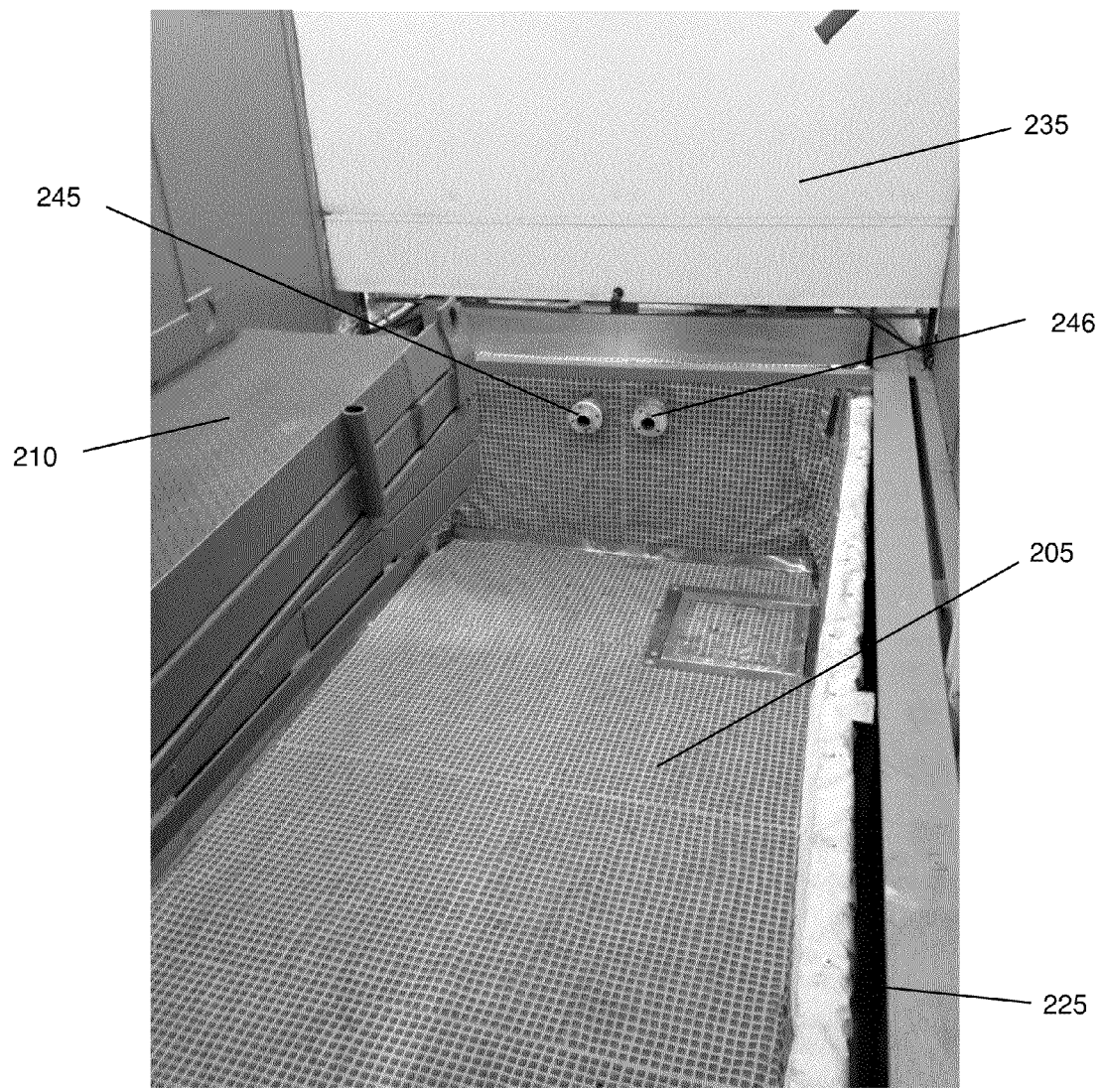
FIG. 7B: Empty Swimming Apparatus

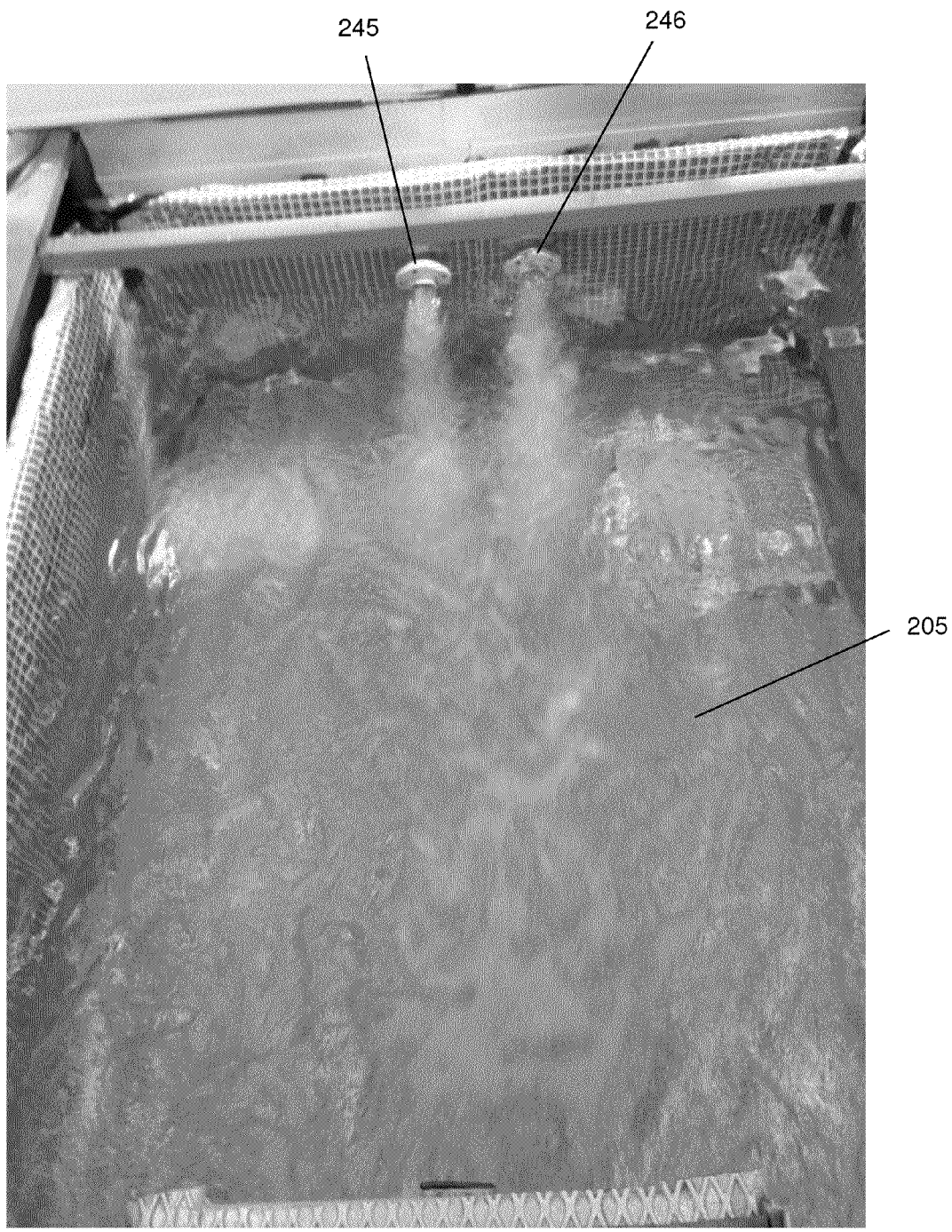
FIG 7C: Water Jets in Action in the Marine Cell.

FIG 7D: Swimming and Water Jogging in the Marine Cell.
205

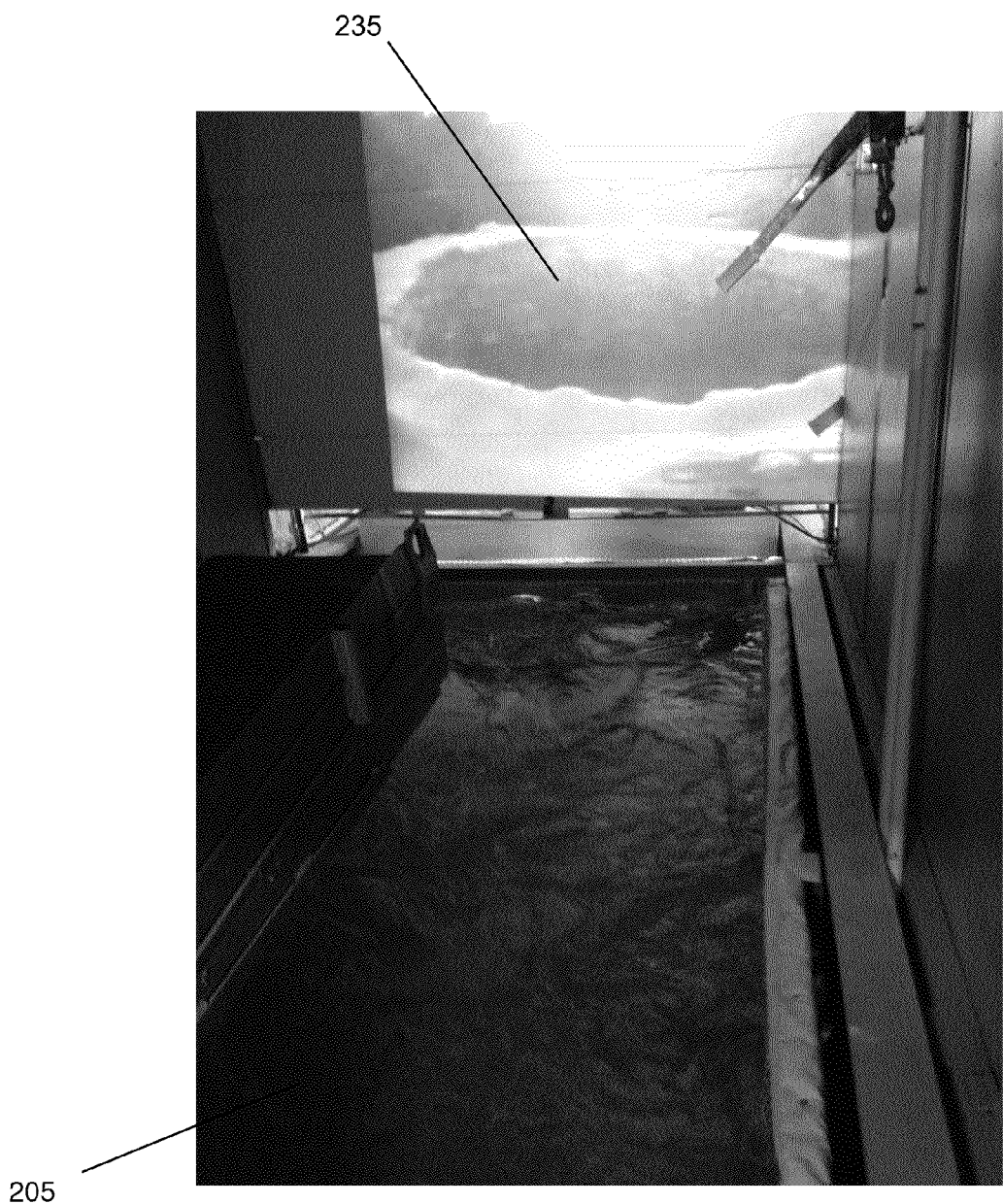
FIG 7E: Projected Screen in the Marine Cell.

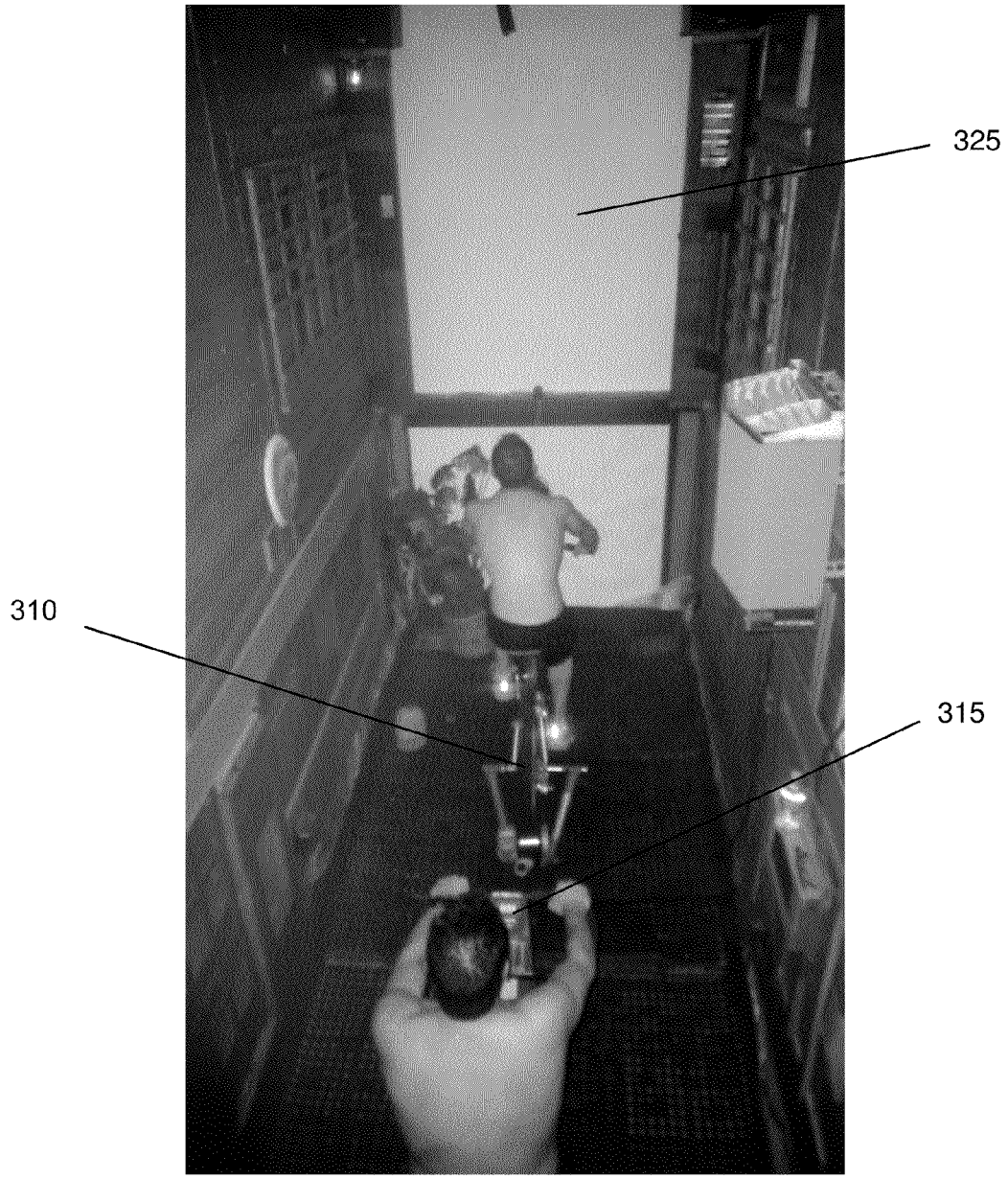
FIG. 8B: Subjects in Tropical Cell

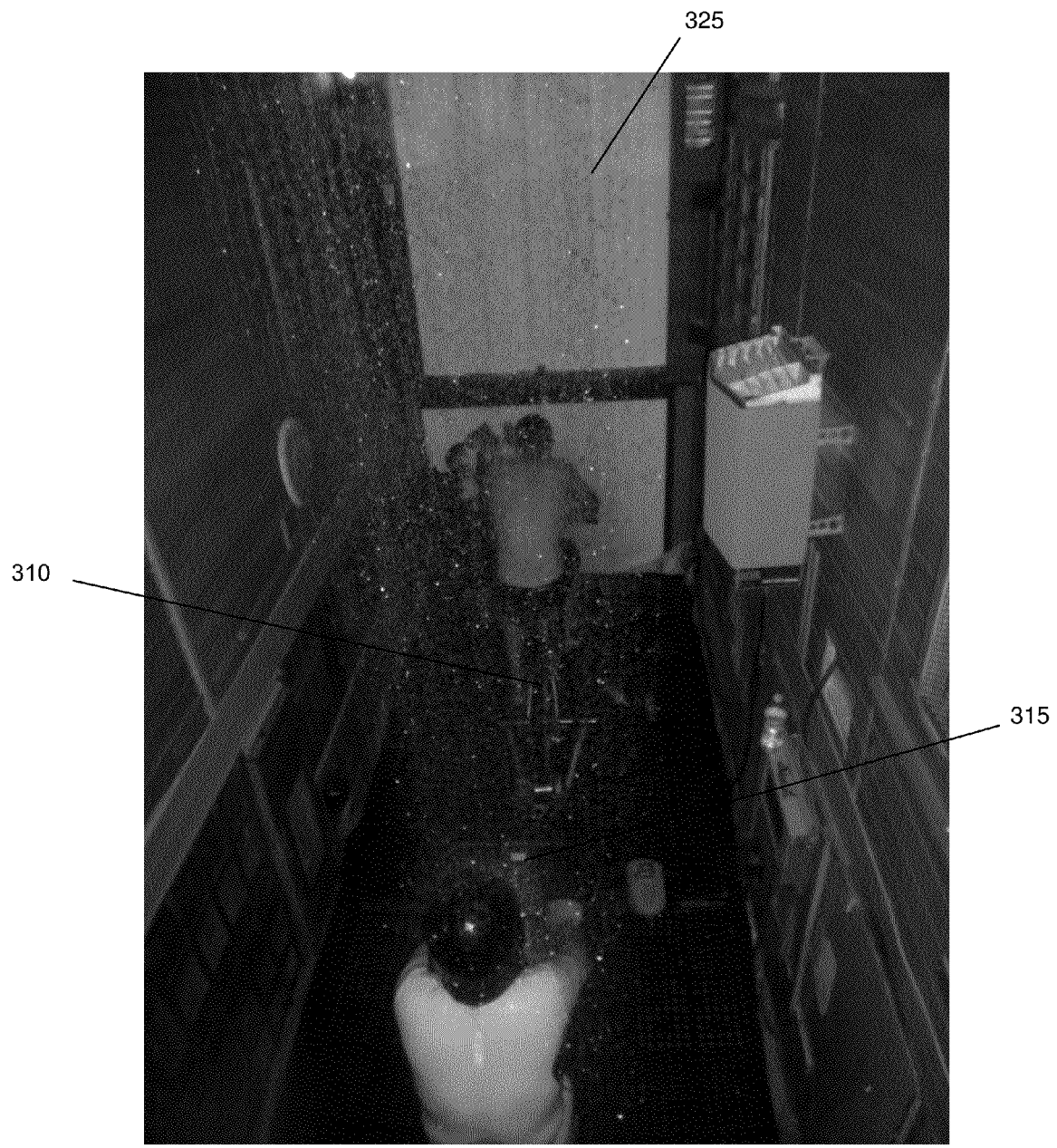
FIG. 8C: Subjects in Tropical Cell

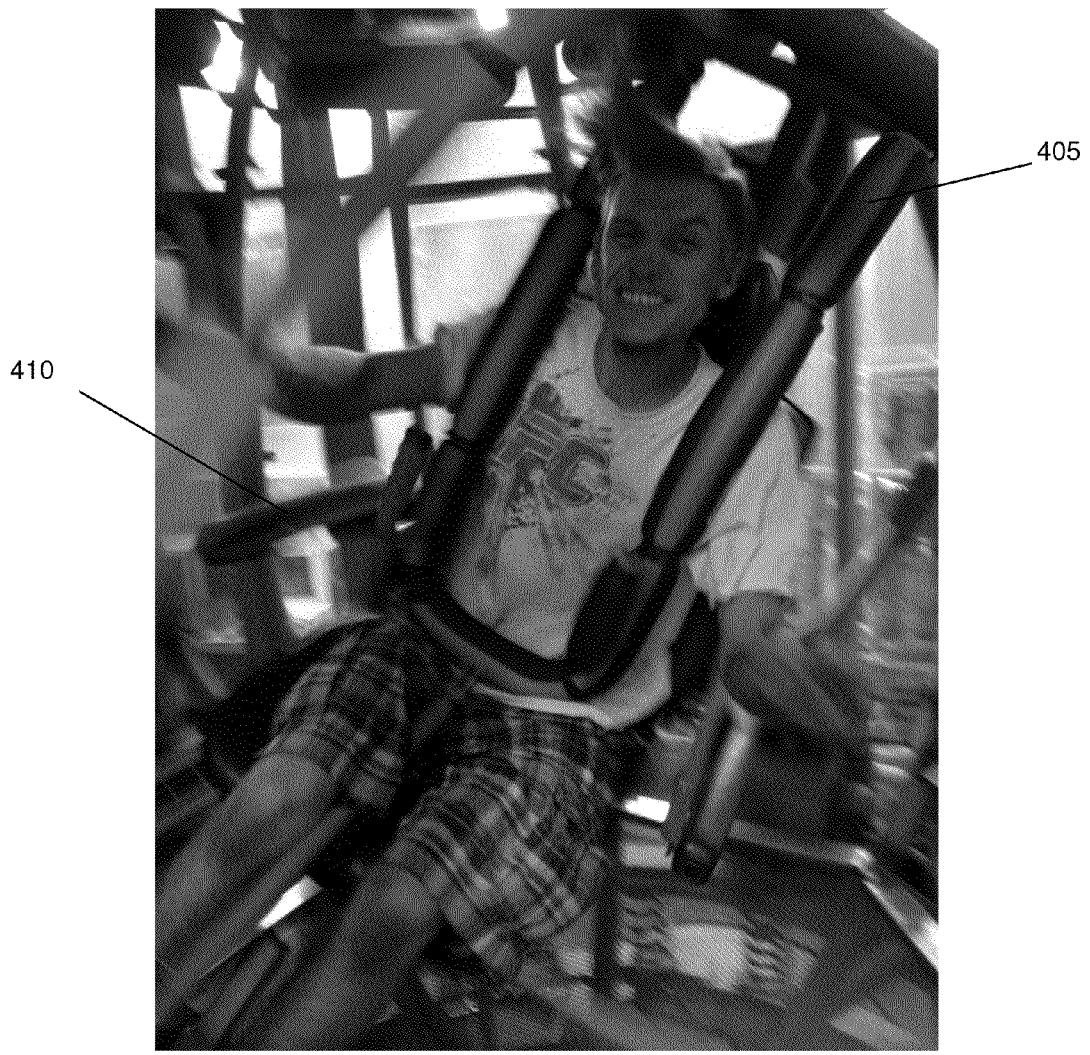
FIG. 9C: Subject seated in Gyroscope

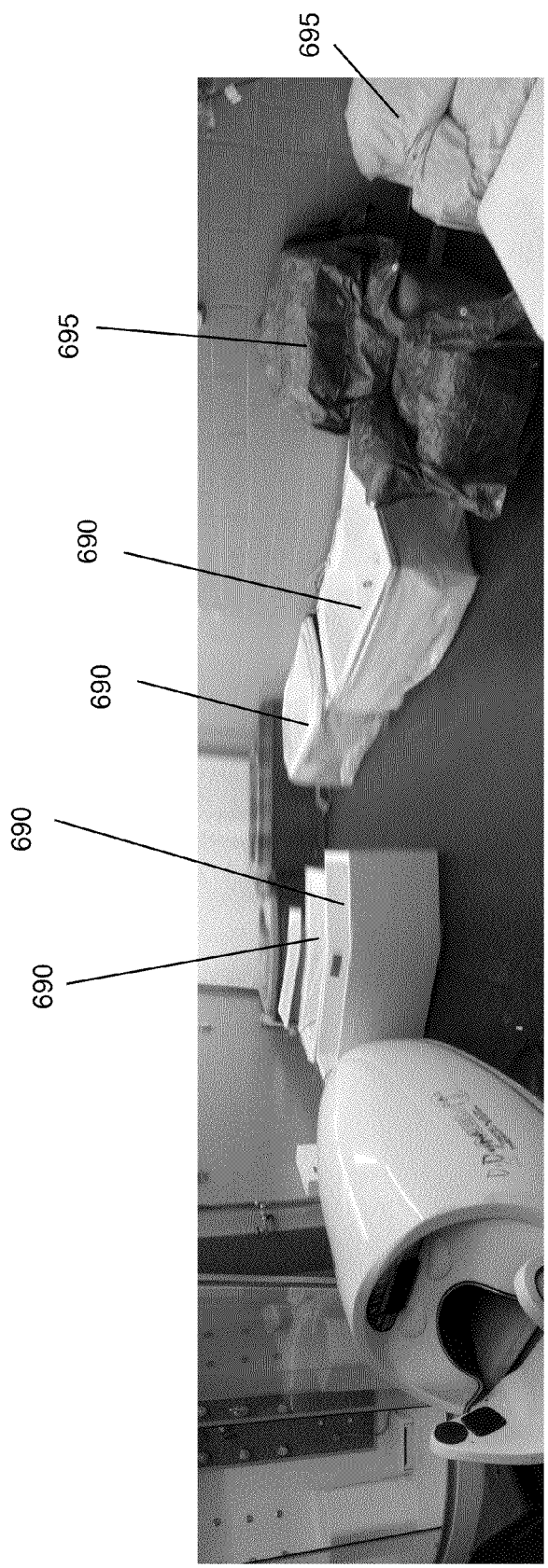
FIG. 10A: Ketone Inducing Soaking System (KISS)

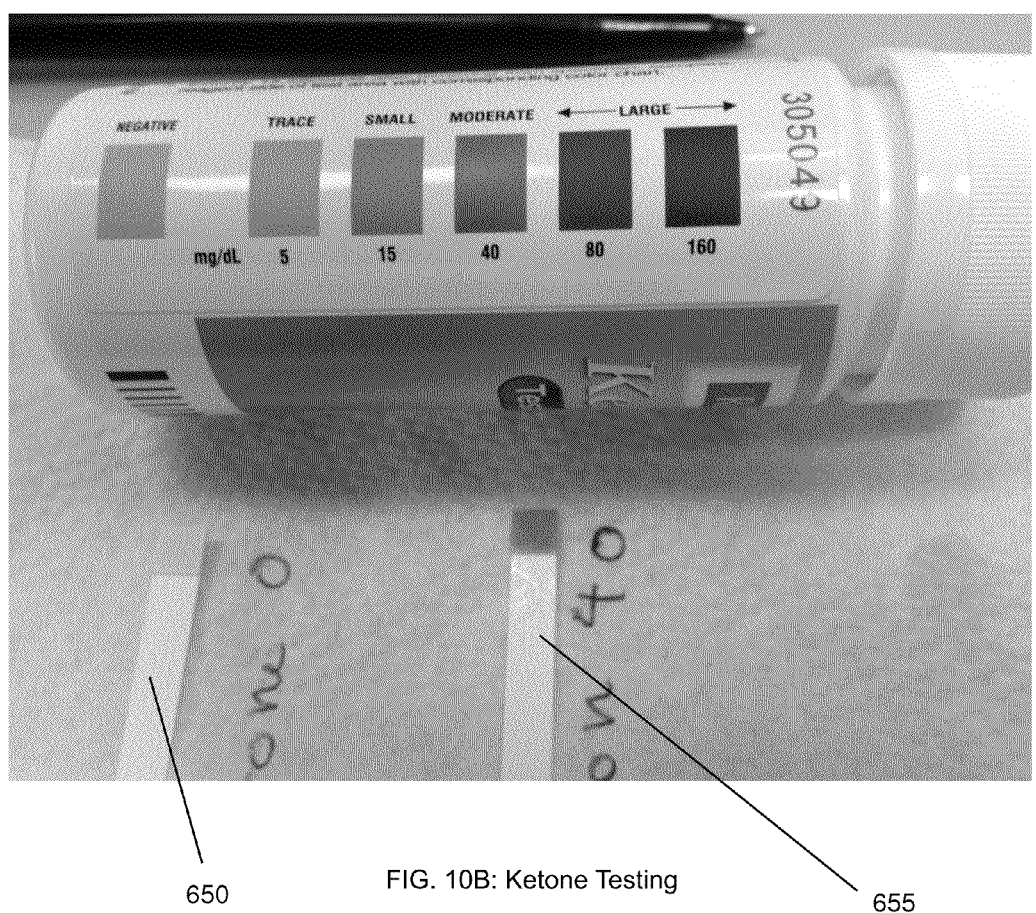
FIG. 10B: Ketone Testing

Tri-Athlon Training Indoor Machine (Tri-A-Trim)
The TRI-EX
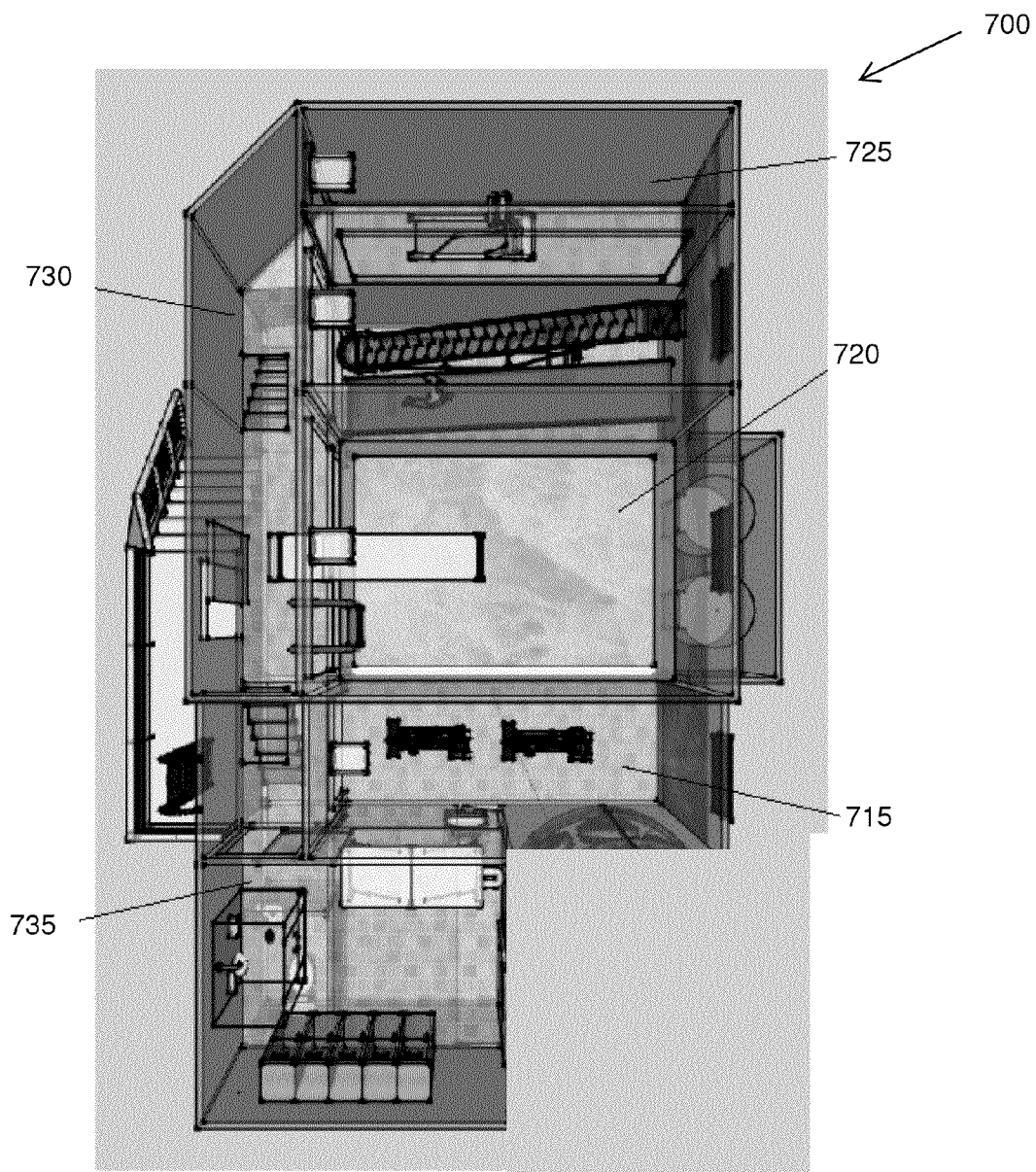
FIG 11: The Tri-Ex / Tri Athlon Training Indoor Machine

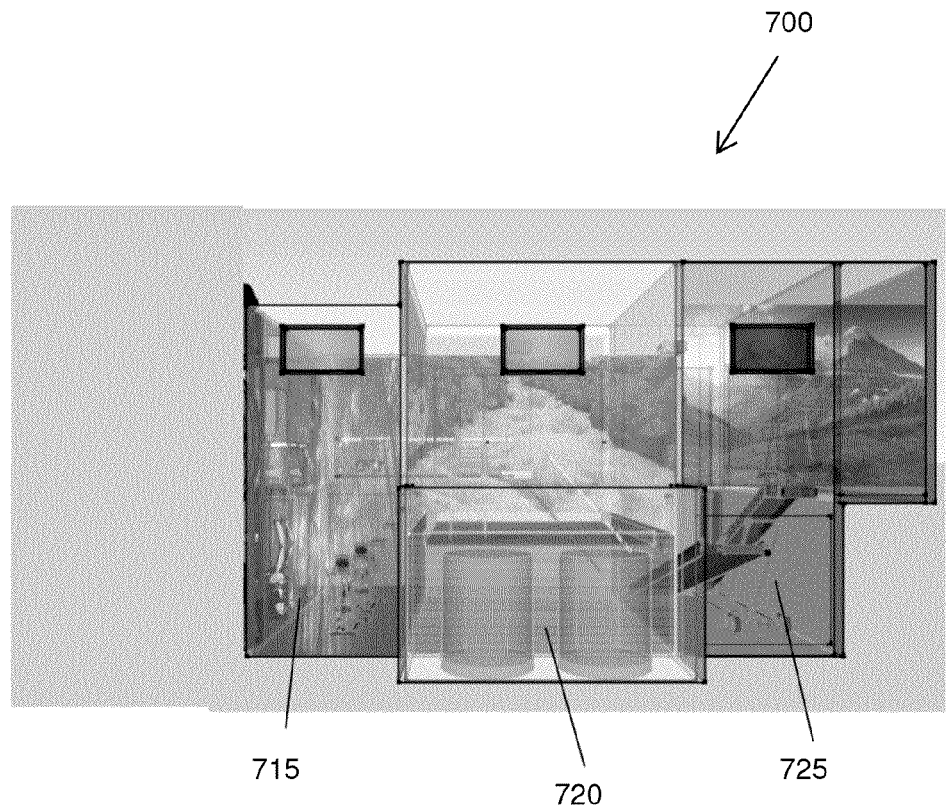
FIG 12: Tri-Ex / Tri Athlon Training Indoor Machine

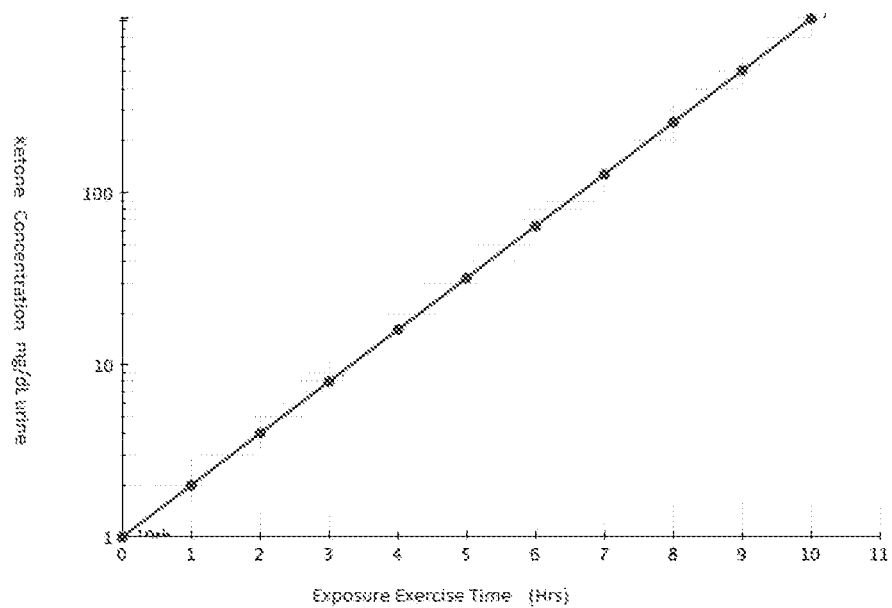
FIG. 13 [[15]]
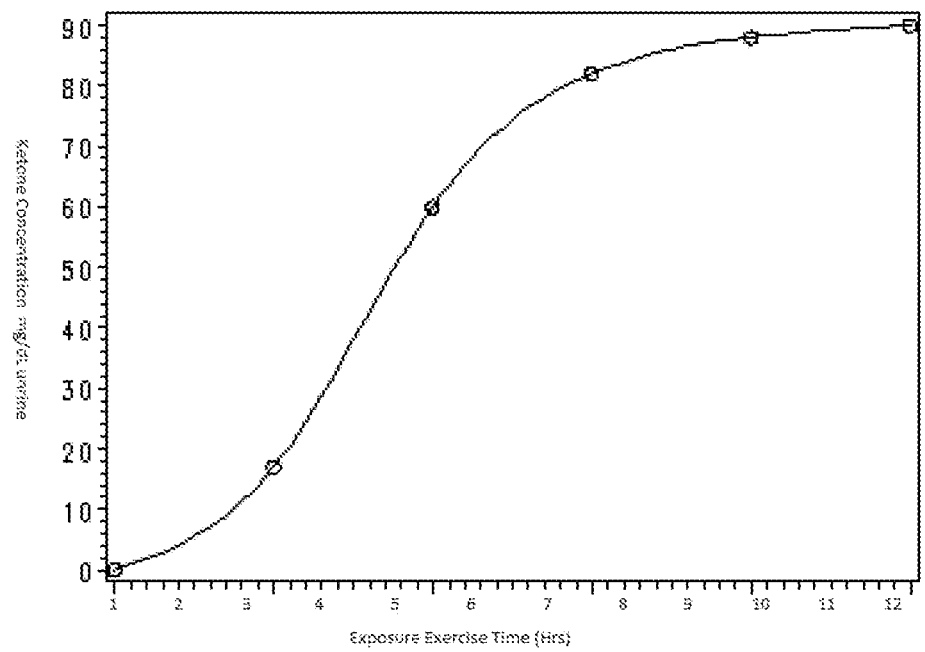
FIG. 14 [[16]]

EXERCISE CELL, KETOSIS/WEIGHT LOSS INDUCING EXERCISE MACHINE (KWIEM) KETOSIS INDUCING APPARATUS (KIA)

BACKGROUND

There is an overwhelming obesity problem in the United States of America and around the globe. This problem is caused mainly by lack of energy expenditure from the human body. Energy expenditure in the form of exercise (mobility) and environmental adaptation has shifted dramatically in favor of energy saving, in the form of fat preservation in human adipose tissue contributing to obesity of the human body. The solution of this problem has to focus on increasing energy expenditure. This can be achieved by increasing exercise mobility, and increasing environmental adaptation by increasing exposure of human body to extreme variations of hot, cold, rain, wind, water and humidity.

Unfortunately, the current solutions do not address the problem of obesity in that manner, hence, the extreme failure of the current solutions in solving the obesity problem. The current solutions focus on surgically interrupting the digestive system in the form of gastric bypass, lap band, or stomach sleeve exposing the human body to surgical complications. The second solution comes in the form of prescribed medications as appetite suppressants, fat absorption blockers, etc. These medications have multiple side effects and many of them have been removed from the market because they cause more harm than benefit. The third solution comes from alternative medicine including over the counter drugs, dietary supplements, and different recipes and potions which is mostly ineffective and costly. The fourth solution comes from exercise gyms and health clubs. Which, despite the fact they address the mobility problem they fall short of achieving any significant results because of the lack of intensity and endurance.

The human body very effectively maintains its core temperature within very narrow limits, as the cells of the body need to be within a certain temperature range for them to function properly. This mechanism of Thermal Regulation is called Thermal Homeostasis this means the body core temperature always stays within a very narrow range around 98° Fahrenheit. When the body is exposed to cold temperatures it generates more heat to combat the cold and maintain its temperature up to 98° Fahrenheit. When the body is exposed to a hot environment the body spends energy to cool itself down to 98° Fahrenheit. This tight Thermal Regulation System expend tremendous amount of energy in both directions namely to effect heating or cooling of the body. Hence it demands that every cell in the body participate (exercise). For example:

Muscle cells: by short repetitive contractions (shivering) create more heat to warm the body in a cold exposure.
Skin cells: in the sweat glands produce sweat and through evaporation will cool the body in a hot environment.
Blood vessels cells: lose heat by vasodilatation in hot environment and preserve heat by vasoconstriction in cold environment.
Solid organ cells: for example, liver, kidney and brain etc. . . . will increase or decrease the metabolic rate in response to increase or decrease of environmental temperature.

In short, every cell in the human body will participate (exercise) in response to body exposure to excessive heat or cold environment; hence the term Cellular Exercise.

As used herein, cellular exercise is activity that takes place inside an exercise cell. It is so called because, (i) the activity takes place inside a steel environment cell, and (ii) the activity stimulates the effort (exertion) by all human body cells.

BRIEF SUMMARY

Aspects of the present invention, the Sequential Environment Exercise Cells (SEEC), provide an effective solution to the obesity problem. By intensifying the energy expenditure in a short period of time through extreme exercise and extreme sequential environmental exposure (exposure to sequence of hot, cold, rain, wind, water and humidity), one can achieve the highest degree of metabolic stimulation and fat burning, resulting in the highest degree of weight loss in the shortest amount of time by physical natural means through application of Cellular Exercise in Exercise Cells. Other aspects of the invention will utilize exercise cells to train athletes for endurance rather than focusing on weight loss.

In one embodiment, cellular exercise will typically take place in a special outlet facility called a Fat Burn Center (FBC). Each Fat Burn Center will contain multiple Sequential Environment Exercise Cells (SEEC) also known as Fat Burn Stations (FBS). Each FBS will comprise multiple exercise cells, but may include at least one exercise cell.

If the Fat Burn Station consists of one exercise cell it will be called:

| Mono-Ex-Cell | 1 exercise cell |

If the Fat Burn Station consists of multiple exercise cells it will be called according to the number of the exercise cells, for example:

| Bi-Ex-Cell | 2 exercise cells |
| Tri-Ex-Cell | 3 exercise cells |
| Tetra-Ex-Cell | 4 exercise cells |
| Penta-Ex-Cell | 5 exercise cells |
| Hexa-Ex-Cell | 6 exercise cells |
| Septa-Ex-Cell | 7 exercise cells |
| Octa-Ex-Cell | 8 exercise cells |
| Dexa-Ex-Cell | 10 exercise cells |

And so on it goes, describing the number of different exercise cells or different environments comprising the FBS.

In one embodiment, a plurality of 4 exercise cells, or Tetra-Ex-Cell, are provided, each cell simulating a natural environment. Typical structural elements include four sequential environment cells with a control area and transition area:

In one embodiment, a mountain climbing exercise cell is provided having a controlled mountain room temperature, typically between −20° and 40° Fahrenheit. The mountain climbing cell further comprises an exercise apparatus and a projector, where the projector is configured to show images on a screen or closed video glasses screen in view of a person utilizing said exercise apparatus. Typically, the exercise apparatus is an incline with a conveyor to simulate climbing on a mountain path. Typically, a freezer unit is used to create a cold environment in the cell. Alternative environments include a hot mountain exercise environment, and alternative exercise apparatus would include a mountain bike, treadmill or other similar types of exercise equipment.

In another embodiment, a swimming cell is provided having water at a controlled temperature, typically between 50° and 90° Fahrenheit. The swimming cell has a resistance swimming apparatus enabling a person to swim in place. In one embodiment, the swimming current is induced by mechanical pumps to provide different current speeds enabling different swimming skills by the users. In yet another embodiment, on the upper half of the swimming cell, a platform and a tension line provides exercise resistance to simulate a sky climb. Further, a projector is configured to show images on a screen or closed video glasses screen in view of a person utilizing said exercise apparatus. Still further, other water exercising apparatus and sky climb apparatus may be utilized.

In yet another embodiment, a rain forest cell is provided having a controlled forest room temperature, typically between 85° and 135° Fahrenheit. The rain forest cell typically has a plurality of shower heads, a heating element, a projector and an exercise apparatus. The shower heads are configured for introducing water to said rain forest cell to simulate rain. The heating element regulates the controlled forest room temperature and creates a high humidity environment. The projector is configured to show images on a screen or closed video glasses screen in view of a person utilizing said exercise apparatus. The exercise apparatus typically comprises an incline with a conveyor to simulate climbing on a mountain path or a stationary exercise bike; however, other alternative exercise equipment can also be used.

In still another embodiment, a space cell is provided having a controlled space room temperature, typically between 85° and 135° Fahrenheit. The space cell has a plurality fans, a heating element, a gyroscope and a projector connected to cord or wireless video glasses to project a space environment. The gyroscope is sized to contain a user and configured for imparting rotational movement and vertical movement to the user's body.

In another embodiment, a control area is provided that comprises one or more displays coupled to cameras located in each of the exercise cells so that an operator may monitor the users exercising in each of the cell. The control area may comprise a plurality of cell controls for controlling the operation of each cell such as, for example, the wind and gyroscope operation in the space cell, the temperature in each of the exercise cells, the displayed images in the rain forest cell and mountain climbing cell and the duration and amount of rain in the rain forest cell. The control area may further comprise a plurality of user monitors to track health data for each user within the cell, such as, for example, heart rate and body temperature monitoring devices.

A transitional & access area may be provided that includes the pathway connecting different individual exercise cells. It also provides access and preparation to each cell, for example, the user will put on climb boots prior to entering the mountain cell, a wet suit prior to entering the marine cell, or space suit prior to entering the space cell.

In a typical operation, an exercise program is designed for the user or multiple users utilizing one or more of the exercise cells. The user spends a predetermined time in a first designated exercise cell before moving to the next exercise cell in a cell cycle. A cell cycle is comprised of exercise time in one or more exercise cells in succession, for example in one embodiment, a user exercises in each of the four exercise cells for a predetermined time of 15 minutes. Accordingly, the cell cycle for this particular embodiment would be one-hour. In a typical cellular exercise session that may last for eight hours, there would be eight cell cycles.

In another embodiment, a plurality of 3 exercise cells or Tri-Ex-Cell are provided for the purpose of training athletes for triathlon competitions with specific course features and climate requirements. For purposes of this description, the associated utility will be referred to herein as a Tri-Athlon Training Indoor Machine (Tri-A-Trim) or a TRI-EX. In a typical embodiment, a TRI-EX comprises three exercise cells, namely, a swimming cell, cycling cell and running cell, which simulate swimming, cycling, and running of a triathlon in regulated, indoor environment. The cells are replicated to reflect the specific features of this triathlon, for example, temperature of the water during the swimming segment of the course, the temperature and elevation of the cycling course, and the temperature and elevation of the running course. In this context, attention is focused on the athletic performance of the triathlete rather than the weight loss aspect of the human subject. Accordingly, no specific attention is devoted to either Ketosis or fasting and preparation prior to athletic performance. Rather, attention is focused on the endurance of the athlete and the acquiring of the experience of the specific features of the triathlon course.

The foregoing and other features, utilities and advantages of the invention will be apparent from the following more particular description of various embodiments of the invention as illustrated in the accompanying drawings and claims.

BRIEF DESCRIPTION OF THE DRAWINGS

FIG. 10B illustrates ketone testing using ketone strips;

FIG. 11 illustrates a top view of one embodiment of a Tri-Ex/Tri Athlon Training Indoor Machine multi-cell exercise environment having three exercise cells;

FIG. 12 shows a front cut-away view of the Tri-Ex/Tri Athlon Training Indoor Machine of FIG. 12;

FIG. 13 illustrates what the relationship between exercise time exposure and the development of the Ketosis state does not look like; and FIG. 14 illustrates the S-shaped curve relationship between exercise time exposure and the development of the Ketosis state.

BRIEF DESCRIPTION

Figure 1:
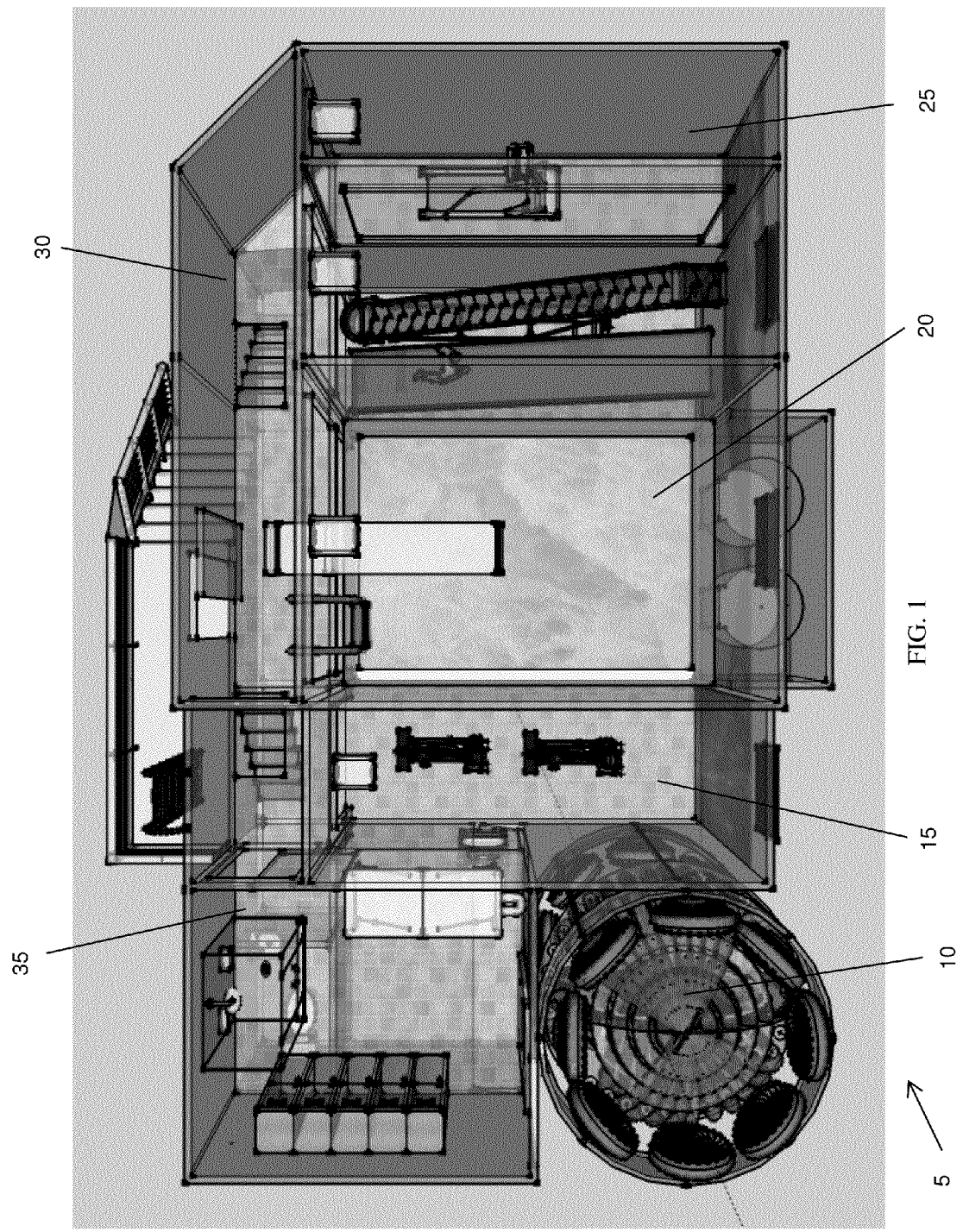
FIG. 1 illustrates a top view of one embodiment of a Quadrex multi-cell exercise environment (Ketosis/Weight Loss Inducing Exercise Machine or KWIEM for short) having four exercise cells in accordance with the illustrated invention.
Figure 2:
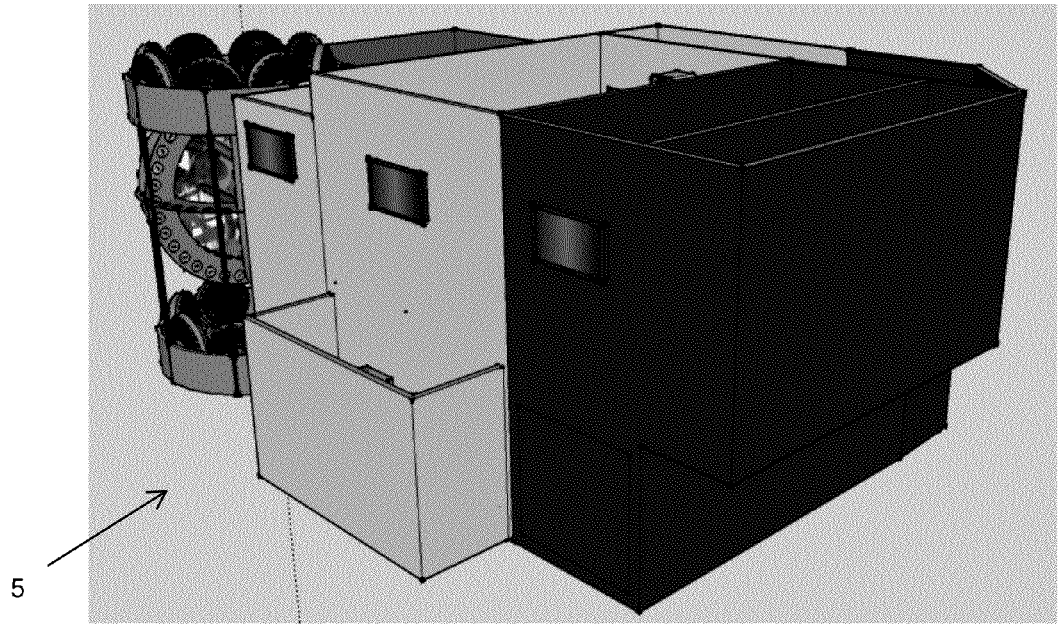
FIG. 2 illustrates a front perspective view of a Quadrex multi-cell exercise environment of FIG. 1.
Figure 3:
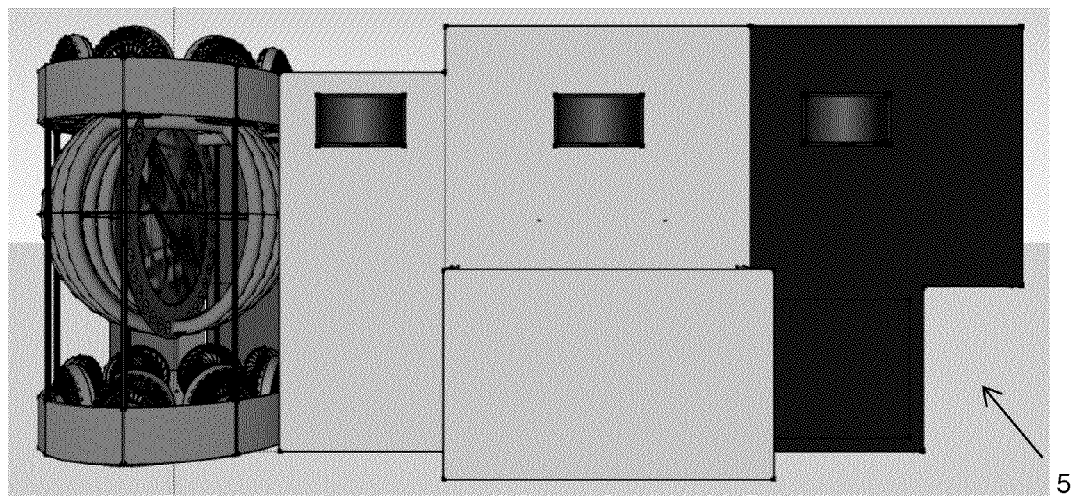
FIG. 3 illustrates a front view of a Quadrex multi-cell exercise environment of FIG. 1.
Figure 4:
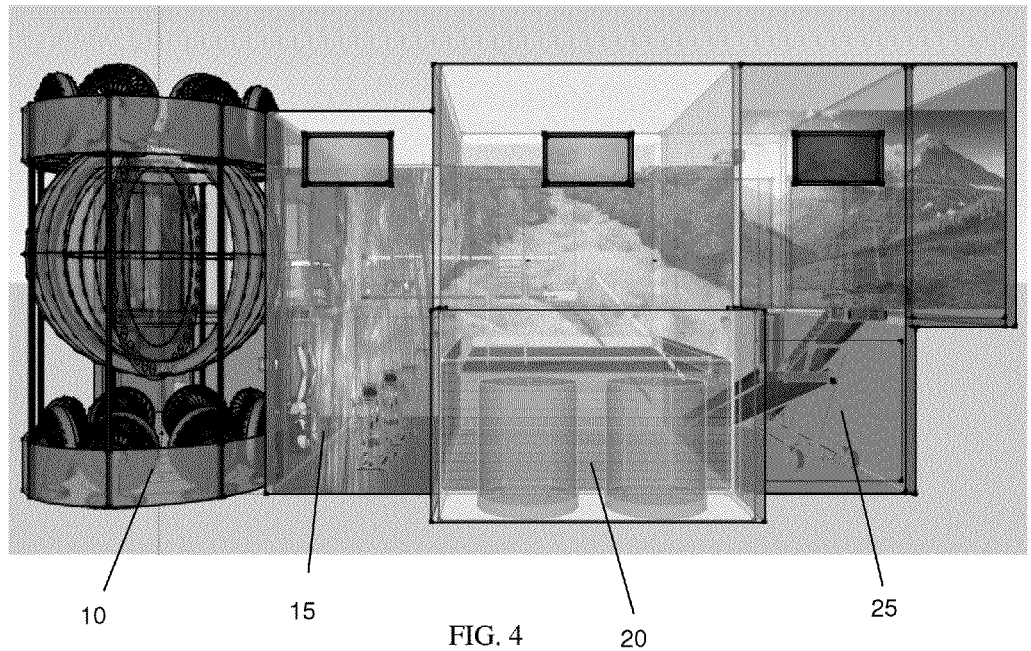
FIG. 4 illustrates a front cut-away view of a Quadrex multi-cell exercise environment of FIG. 1.
Figure 5:
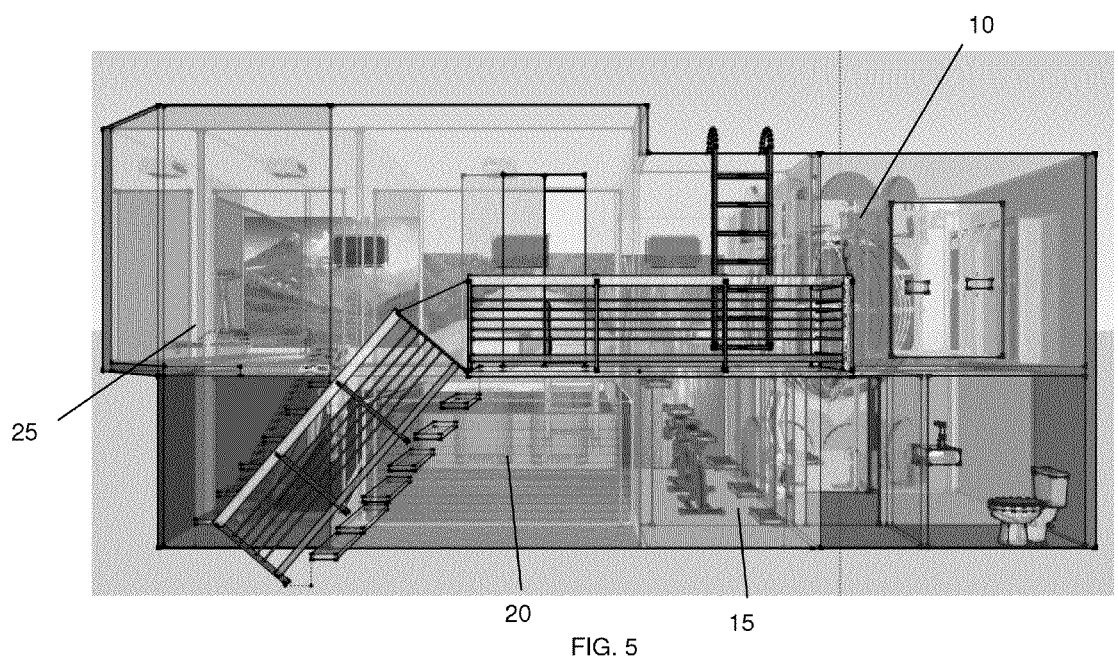
FIG. 5 illustrates a rear cut-away view of a Quadrex multi-cell exercise environment of FIG. 1.

In the following description, numerous specific details are set forth, such as examples of specific shapes, components etc., in order to provide a thorough understanding of the present invention. It will be apparent, however, to one skilled in the art that the present invention may be practiced without these specific details. In other instances, well known components or methods have not been described in detail, but rather in general terms in order to avoid unnecessarily obscuring the present invention. Thus, the specific details set forth are merely exemplary. The specific details may be varied from and still be contemplated to be within the spirit and scope of the present invention.

Reference to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices. It is further contemplated within the scope of this invention that calculations can also be done mentally, manually or using processes other than electronic.

Description of Ketosis and its Application to Weight Loss

Ketosis is the process by which fat breaks down in the human body. When human adipose tissue exceeds normal values (about 10-15% of the human adult ideal body weight), it contributes to obesity. To reduce obesity, and significant to the process of the present invention, adipose tissue fatty acids are broken into Ketones. Ketones are intracellularly combined with oxygen to form carbon dioxide, water, and energy, which is then transformed (burned) by the human body. Other portions of the Ketones are eliminated passively via exhalation and urination. Ketosis reduces the quantity of adipose tissue in the human body, thereby reducing obesity, and affecting weight loss.

The Ketosis/Weight loss Inducing Exercise Machine (KWIEM) of the present invention defines, as its primary focus, the process of Ketosis, which is the first step of human fat transformation. Coupled with Thermal Kinetic energy expenditure in an enclosed environment (exercise cells), Ketones are also intracellularly combined with oxygen to form carbon dioxide, water, and energy, thereby multiplying the effect of just exercise alone and inducing significant and rapid weight loss. The invention described herein emphasizes the fact that, despite the existence of many alternative methods of weight loss/fat reduction methods available (e.g. surgical, diet, exercise, nutritional, etc.), all methods lead to ketosis. Hence, regardless of the method used to achieve weight loss, if it does not end in Ketosis it will be deemed an exercise in futility.

One advantage of using Ketosis as a proxy of the weight loss process is the fact that the ketotic state is easily measured. The monitoring of Ketosis typically, involves simple use of urine dip strips coated with color indicators, which may be easily performed by anyone in any environment.

The current concept of utilizing a traditional weighing scale to monitor weight loss is inadequate. It is theorized that in order to rid the body of one-pound of fat, the body must expend an output of energy equivalent to 3,500 calories. However, the utilization of the (in vitro) theoretical formula which states, in simple terms, that in order for a human body to lose one-pound of fat, it needs to burn 3,500 calories proves inadequate to describe actual (in vivo) physiological conditions related to weight loss. Significantly, this theory assumes that each molecule of fat must end up being burned to carbon dioxide, water, and energy in order to shed it from the human body.

However, in real life, each molecule of fatty acid breaks enzymatically to thousands of Ketone molecules by the process of ketosis. These ketone molecules then, in turn, exit the human body in three pathways: the first pathway, a significant amount of these Ketones are expelled from the human body passively via the respiratory system in the exhaled air as Ketones without being burned to carbon dioxide, water, and energy. In a second pathway, the urinary system expels ketones in the urinary output in the form of Ketones, with the energy still captured inside them. The third pathway is via the intracellular Kreb's cycle to be combined with oxygen (burned) to form carbon dioxide, water, and energy.

That is to say, for each one-pound of fat, it is not required to burn the total of 3,500 calories to rid the body of this pound of fat. Rather, the body needs to burn only a portion of the 3,500 calories to rid the body of the total of the 3,500 calories as the rest or the other portion will be removed passively from the body without being burned. As such, if human body is in the state of Ketosis, a subject needs only to do half the work to get rid of the entire pound of fat versus when the human body is not in the state of Ketosis it needs to do the whole amount of work (3,500 calories) to get rid of one pound of fat. In other words, when a human body is in the state of Ketosis, the adipose fatty tissue weight loss reduction is doubled for each energy output unit.

The following description is intended to illustrate a plurality of exercise cells for use in an exercise program or session. For purposes of the description, a session is typically eight hours in length and a cell cycle is typically one hour in length. However, the length of time for each session and cell cycle is intended session for illustrative purposes only. Accordingly, one of ordinary skill in the art will appreciate that a session and/or cell cycle may differ from the illustrated amount to facilitate a particular work-out program.

Ketosis/Weight Loss Inducing Exercise Machine (KWIEM)

Typically, before the subject is introduced to The Ketosis/Weight loss Inducing Exercise Machine (KWIEM), the subject will undergo a prep process (Ketone Inducing Prep or KIP for short), which is described more thoroughly herein. In one particular embodiment, KIP Day 1 involves: (i) Colon Flush to remove unnecessary waste from the colon, and (ii) Carbo Flush Fasting (36 hours of medically supported fasting) to consume all carbohydrates in the body and prepare the body for the Ketotic state. Continuing with the illustrated embodiment contained herein, Day 2 provides two possible pathways for realizing the exponential benefits of placing the body into a Ketotic state for weight loss: KWIEM or (Ketosis Inducing Machine) (KIM) for short as described in the paragraphs that follow, or Ketosis Inducing Soaking System (KISS) as described in the portion on the process.

Ketosis/Weight Loss Inducing Exercise Machine (KWIEM) a.k.a. Quadrex Illustrated in FIGS. 1-5

In the illustrated embodiment of FIGS. 1 through 5, the KWIEM or Quadrex is illustrated and described. In the illustrated embodiment of FIG. 1, showing a top view of the Quadrex with the roof removed to allow viewing of the interior, the illustrated example of the Quadrex comprises four exercise cells, or Tetra-Ex-Cell, each cell simulating a natural environment. In the illustrated embodiment, the Quadrex comprises four sequential environment cells—a space cell 10, a rain forest cell 15, a swimming cell 20 and a mountain cell 25, a control area 35 and a transition area 30, described in greater detail in the paragraphs that follow. As shown in FIGS. 2-5, the cells are self-contained and environmentally segregated from adjacent cells. Such a segregated construction allows the temperature and environment of each cell of Quadrex to be individually controlled, adjusted and regulated by different devices and equipment.

In the description of the individual cells that follows, each cell is divided into three elements for purposes of illustrating and describing the cell make-up: the equipment, the environment and the visual. The equipment denotes the underlying physical elements that make up the cell. The environment is the condition, atmosphere and associated surrounding that the equipment creates in the cell that simulates a real world environment. And finally, the visual is the pictorial and graphical projections that add real life to the physical environment and therefore make it feel like the subject is truly immersed within the simulated environment. One of ordinary skill in the art will appreciate that more or less cells may be included without departing from the scope and spirit of the present invention.

Figure 6:
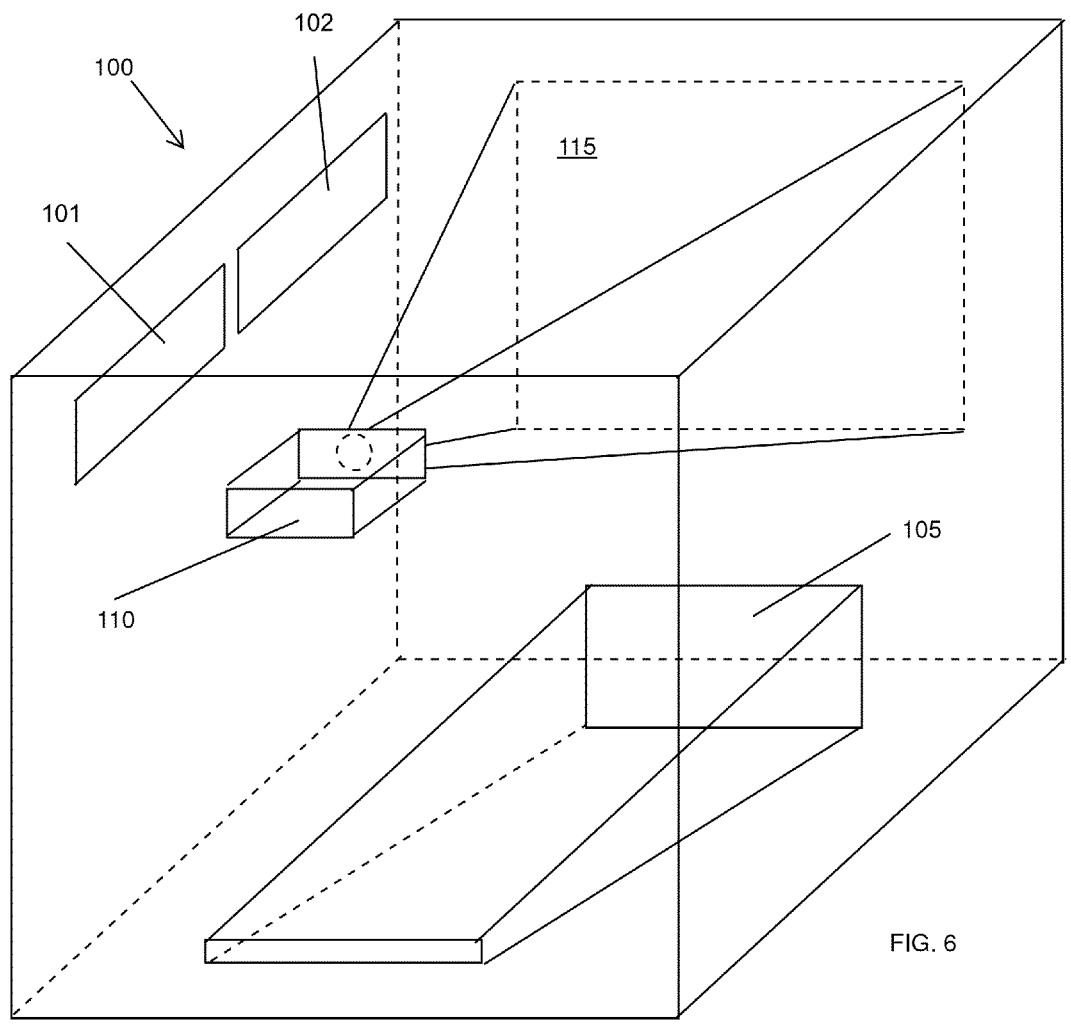
FIG. 6 illustrates a mountain climbing cell for implementing the illustrated embodiment of the present invention.
Figure 6A:
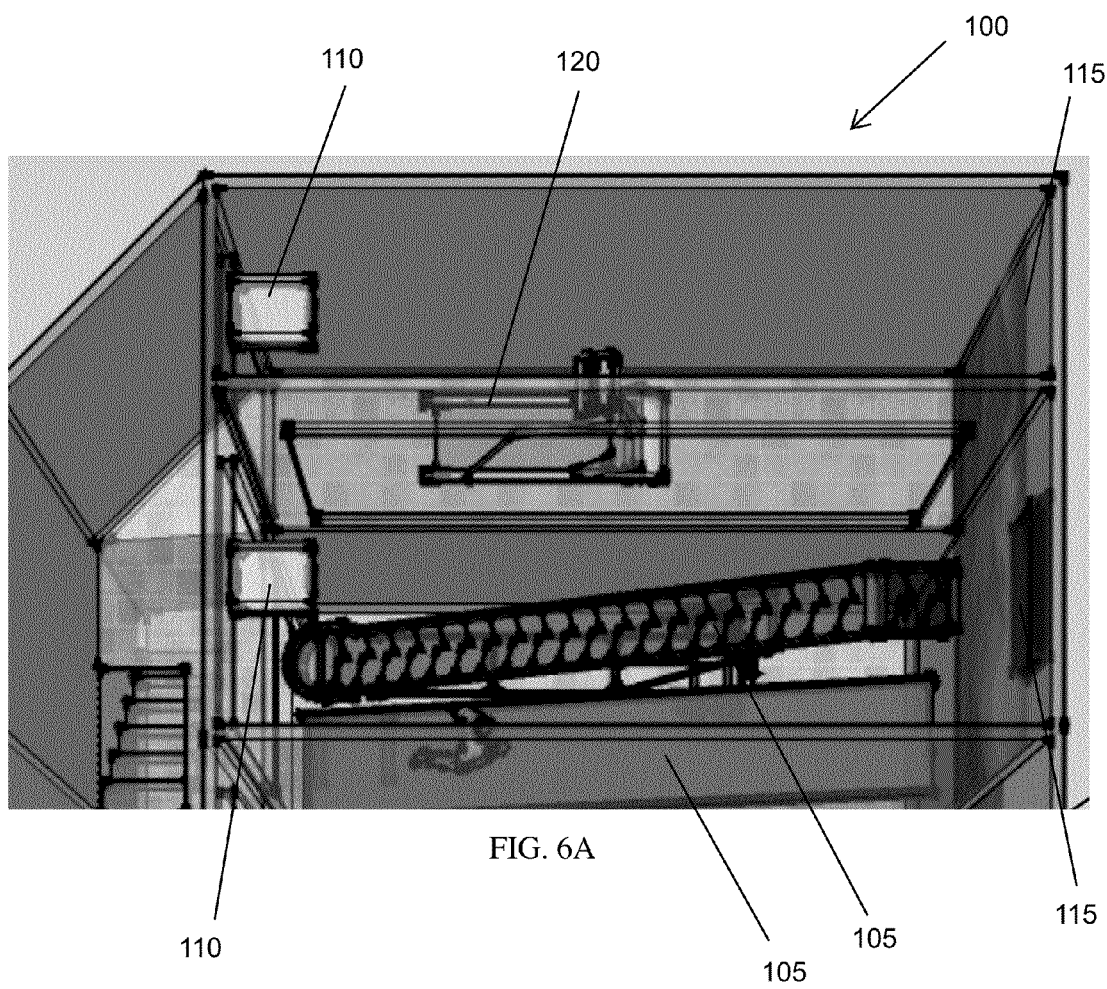
FIG. 6A is a top view of the mountain climbing cell illustrated in FIG. 6.

Mountain Cell/Running Cell Illustrated in FIGS. 6, 6A

Element 1: Equipment
In one embodiment, the mountain cell is comprised of one or more of the following: (i) a 16 footer at 35° high incline conveyor belt configured for simulating hiking, (ii) a conventional high incline treadmill with a 15° fixed incline and up to 15° additional variable incline with a control panel to control the incline and speed to simulate running in mountain, and (iii) an elliptical machine with variable resistance to simulate cross country skiing.
Element 2: Environment
In the illustrated embodiment, a simulated mountain environment is produced by the use of a two (2) one-ton freezer units configured of the temperature inside the mountain cell to −20° Fahrenheit to 40° Fahrenheit, along with multiple wind producing fans to create variable windy conditions on a mountain, for example.
Element 3: Visual
In the illustrated embodiment, the visual element is produced by a video player connected to a projector, projecting onto a screen in front of the mountain cell. Typically, the projector generates activities that take place on a mountain on the front wall of the mountain cell for a subject to see. Also provided is a laptop connected to the internet to video streaming activities in real time that take place in different locations, such as various mountain ranges, around the globe. In another embodiment, cable or satellite television may be connected to the projector to further simulate any number of environments available as television programming.

All three elements working in symmetrical harmony, including the equipment, environment, visual, produce the effect of running, hiking, or cross country skiing in a cold mountain atmosphere. The harmonic operation described engages the subject in a high energy output thermal kinetic exercise with the purpose of producing the state of Ketosis, which further produces the state of weight loss as explained herein.

FIG. 6 illustrates a mountain climbing cell 100. In one embodiment, mountain climbing cell 100 has a two (2) one-ton freezer units 101, 102 to maintain a controlled a mountain room temperature that is typically between −20° and 40° Fahrenheit to simulate the temperatures of a mountain environment. The mountain climbing cell of the illustrated embodiment further comprises an exercise apparatus 105 and a projector 110. Exercise apparatus 105 is illustrated as an incline with a conveyor to simulate climbing on a mountain path, however one of ordinary skill in the art can appreciate that any exercise apparatus may be used without departing from the scope and spirit of the present invention, such as a cross country skiing simulator, an elliptical running device, a stationary bike, or similar apparatus. The projector 110 is configured to show images 115 on a screen in view of a person utilizing exercise apparatus 105. The projector can show images on an open screen or a closed circuit on video glasses.

FIG. 6A illustrates a top view of the mountain climbing cell 100 of FIG. 6, showing potential placement of the exercise apparatus 105, projector 110, images 115 and exercise apparatus 120.

Figure 7:
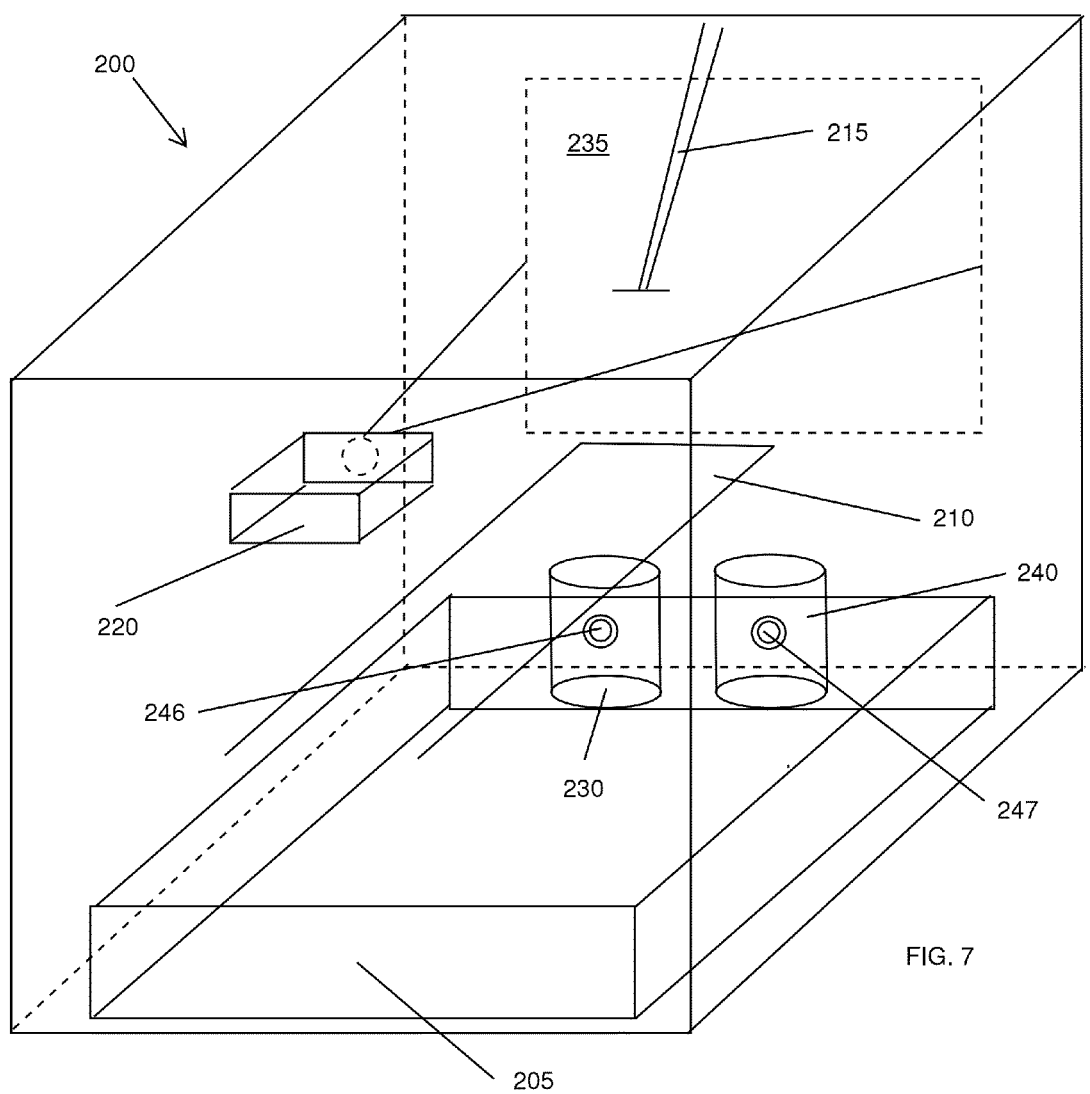
FIG. 7 illustrates a swimming cell for implementing the illustrated embodiment of the present invention.
Figure 7A:
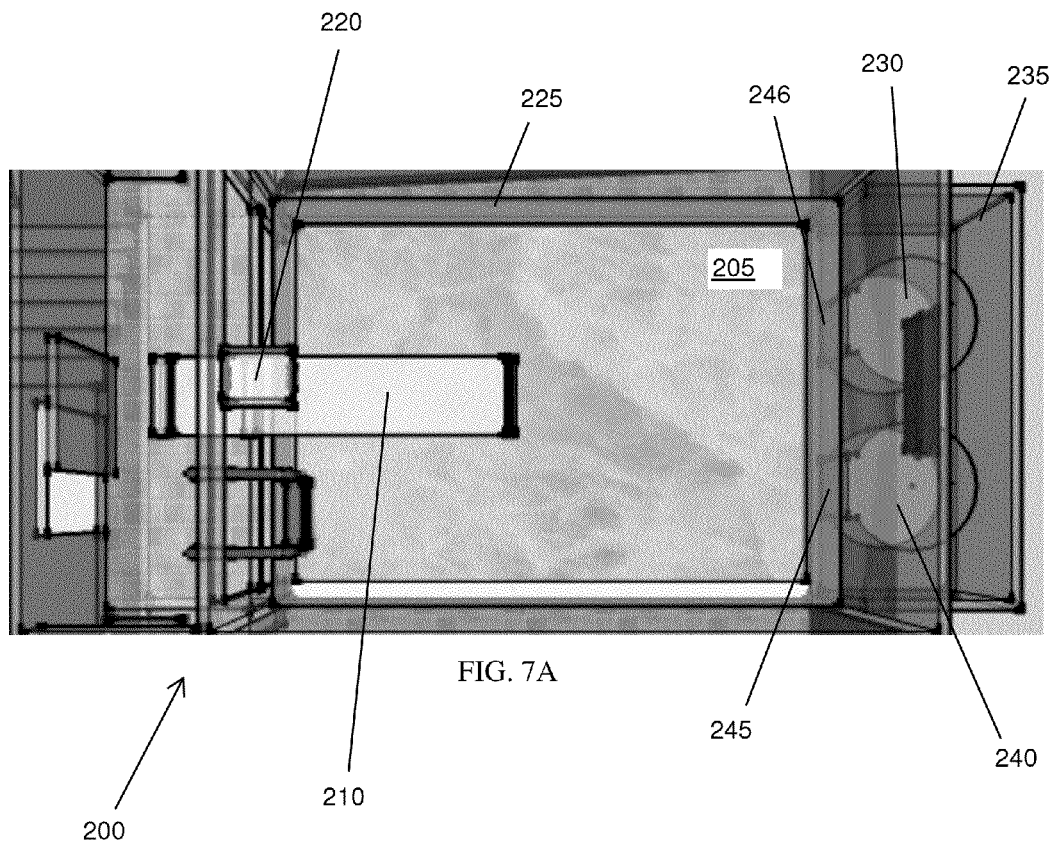
FIG. 7A is a top view of the swimming cell illustrated in FIG. 7.

Marine Environment Cell/Swimming Cell Illustrated in FIGS. 7, 7A

Element 1: Equipment
In the illustrated embodiment, the marine environment cell is comprised of one or more 24'×12'×6.5° swimming pools in a contiguous cell, typically located between a mountain cell and a tropical rain forest cell. The illustrated swimming pool is typically made of leakage proof rust resistant steel elements to withstand the extreme environmental conditions.
Element 2: Environment
Rapids are created within this large pool through two smaller water containments. In the illustrated embodiment, the front containment house provides two 400-gallon per minute pumps that circulate the water between a large pool and a small pool to create a dynamic swimming current that the human subject has to work against to stay in place either by swimming or by water running/walking inside the smaller swimming pool.

Pump equipment to filter the water is added to the front water containment (pump container) along with wind inducing fans to create a windy, raging ocean environment. In the illustrated embodiment, the smaller user pool measures 20'×8'×4', with an open floor area in the back measuring 2'×7.5° to allow water to circulate from the user pool to the large pool.

The illustrated pool is made of leakage proof rust resistant steel elements with standard commercial pool lining to allow a clean and safe use of the pool. In one embodiment, a steel extension simulation a jump board measuring 2'×6' is located on the surface area of the marine environment to allow a platform for sky climbing. Sky climbing subjects a user to a backward pulling force through a first series of elastic ropes and forward pulling forces provided by a second series of elastic ropes. In operation, the human subject to exert resistance to balance between the backward and forward pulling forces, thereby simulating sky climbing.

When immersed within the marine/ocean environment cell, the subject will be acted upon by thermal kinetic forces in the form of cold water swimming/walking/sky climbing with the end results of extreme expenditure of thermal kinetic energy. Such expenditure facilitates Ketosis, which further boosts weight loss as explained herein.

Element 3: Visual

The visual element is produced by a video player connected to a projector, projecting onto a screen in front of the marine environment cell. This projector projects activities that take place in an ocean marine environment in the front of the marine cell. Also provided is a laptop connected to the internet to video streaming activities in real time that take place on different areas, such as open water in various bodies of water around the globe. In another embodiment, cable or satellite television may be connected to the projector to further simulate any number of environments available as television programming.

FIG. 7 illustrates a marine environment cell 200. As shown in the illustrated embodiment, marine environment cell 200 has a resistance swimming apparatus 205 enabling a person to swim in place in water at a controlled water temperature and speed. Typically, the controlled water temperature is between 50° and 90° Fahrenheit. The marine environment cell is also equipped with a sky climb apparatus comprising a platform 210 and a tension line 215 to provide exercise resistance for a user. In operation, a user stands on platform 210. The user is restrained on one side by a plurality of resistance lines (not shown) while pulling on the traction line 215, which is typically a resistance rope. The counteraction of the two activities causes the user to expend energy.

FIG. 7A illustrates a top view of the marine environment cell 200 showing the swimming apparatus 205 in greater detail. Swimming apparatus 205 is placed within a larger water tank 225. Hanging from the ceiling is a projector 220. A first pump 230 is coupled to the swimming tank 205 using piping 246. A second pump 240 is coupled to the swimming tank 205 using piping 245. The two pumps are located in a front water tank 231. In operation, the pumps 230, 240 draw water from the front water tank 231 and pump it under pressure into swimming water tank 205. The pressurized water from the two pumps creates the current that the user swims against.

Figure 8:
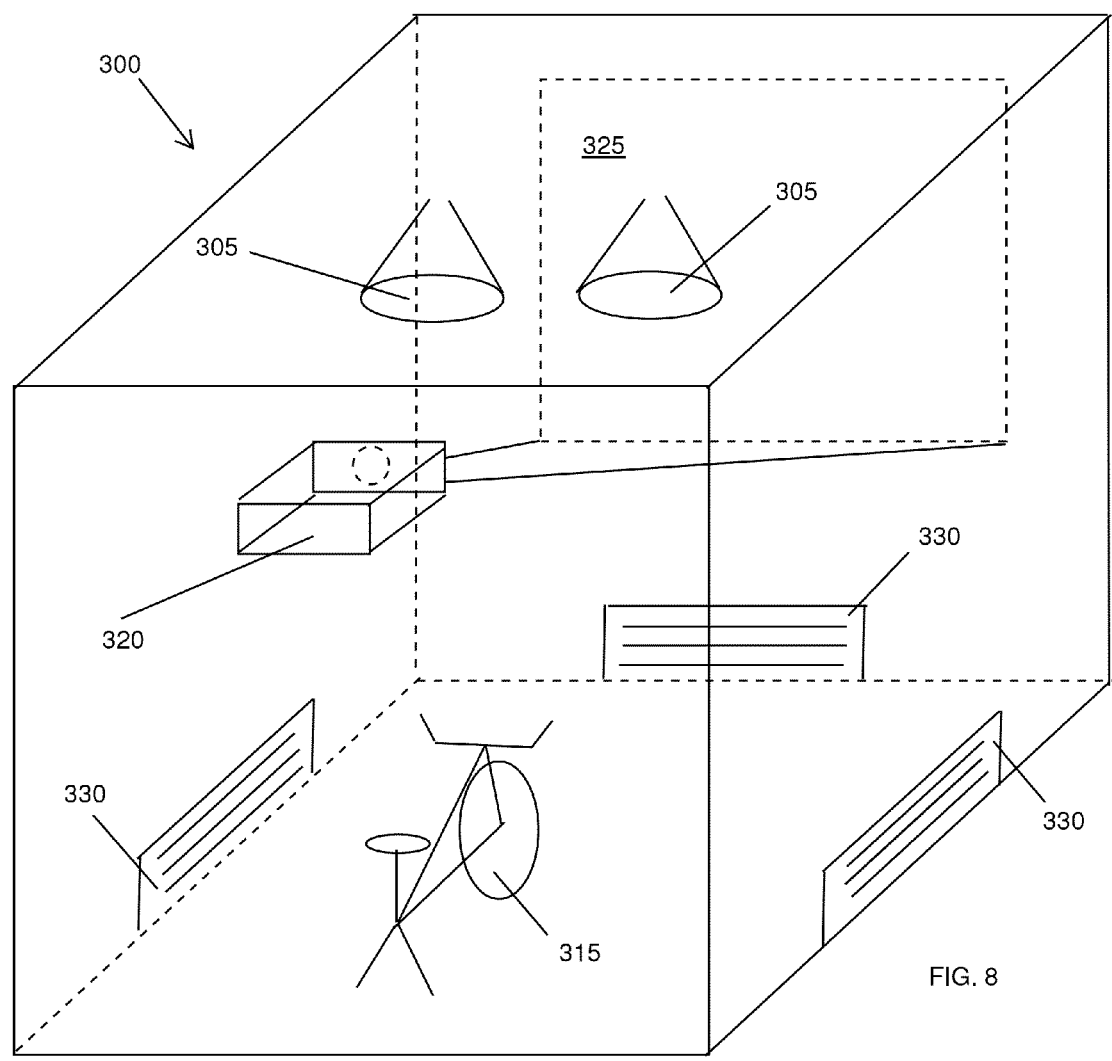
FIG. 8 illustrates a rain forest cell for implementing the illustrated embodiment of the present invention.
Figure 8A:
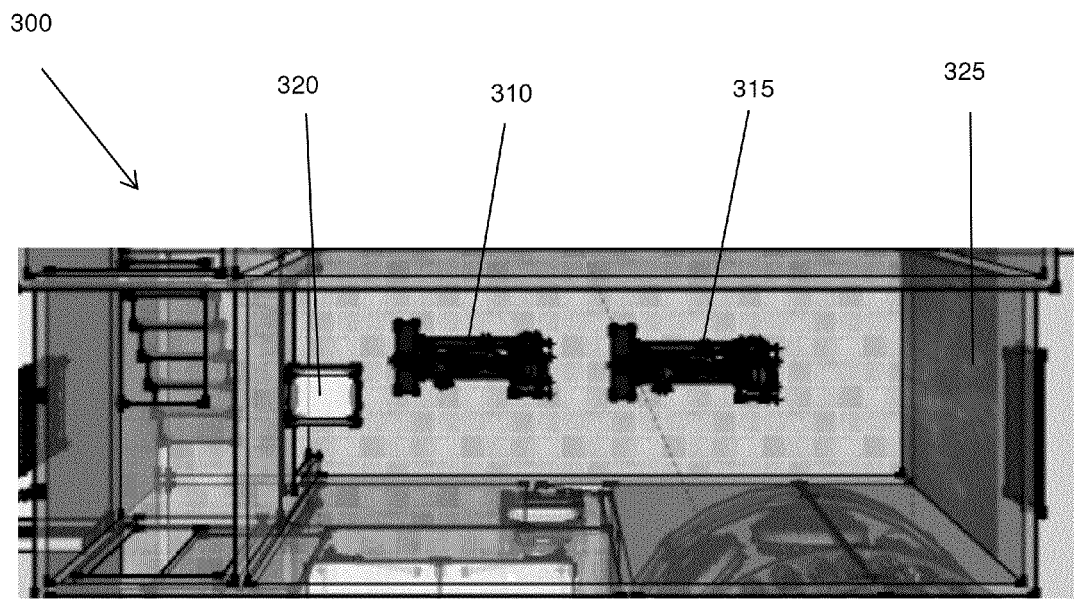
FIG. 8A is a top view of the rain forest cell illustrated in FIG. 8.

Tropical Rain Forest Cell/Cycling Cell Illustrated in FIGS. 8, 8A

Element 1: Equipment

In one embodiment, the tropical rain forest cell is comprised of one stationary bike and one mountain training bike that is suited with mechanical accessory.

Element 2: Environment

In the illustrated embodiment of FIG. 8, multiple heat elements are provided, mounted to the wall similar to a sauna. In addition, a heat inducing machine may be mounted to the wall as well. The temperature rage is typically between 90° and 135° Fahrenheit, or as tolerated by the particular human subject.

Additionally, the rain and humidity are introduced by multiple shower head apparatus mounted to the ceiling and connected to a valve controlled by an electric switch to turn the simulated rain in the tropical rain forest cell on and off as need.

Element 3: Visual

The visual element is produced by a video player connected to a projector, projecting onto a screen in front of the tropical rain forest environment cell. This projector projects activities that take place in a tropical rain forest environment in the front of the cell. Also provided is a laptop connected to the internet to video streaming activities in real time that take place on different areas, such as different rain forest environments in the amazon for example, around the globe. In another embodiment, cable or satellite television may be connected to the projector to further simulate any number of environments available as television programming.

FIG. 8 illustrates a rain forest cell 300. Rain forest cell 300 has a controlled forest room temperature between 85° and 135° Fahrenheit. The rain forest cell 300 is fitted with a plurality of shower heads 305, a projector 320, a plurality of heating elements 330 and an exercise apparatus 315. Exercise apparatus 315 is illustrated as a stationary bike, however, one of ordinary skill in the art will appreciate that any exercise apparatus may be used without departing from the scope and spirit of the present invention, such as a cross country skiing simulator, an elliptical running device, an exercise bike, or similar apparatus.

The shower heads 305 are configured for introducing water to said rain forest cell 300 to simulate rain. The projector 320 is configured to show images 325 on a screen in view of a person utilizing exercise apparatus 310 and 315. The heating elements 330 are configured to introduce heat in the rain forest cell and maintain the controlled forest room temperature. FIG. 8A illustrates a top view of the rain forest cell 100 of FIG. 8, showing potential placement of a pair of exercise apparatus 310, 315, projector 320, and images 325. Exercise apparatus 315 is illustrated as a stationary bicycle and exercise apparatus 310 is illustrated as an exercise bike, however, one of ordinary skill in the art can appreciate that any exercise apparatus may be used without departing from the scope and spirit of the present invention such as an incline with a conveyor to simulate climbing on a mountain path for example.

Figure 9:
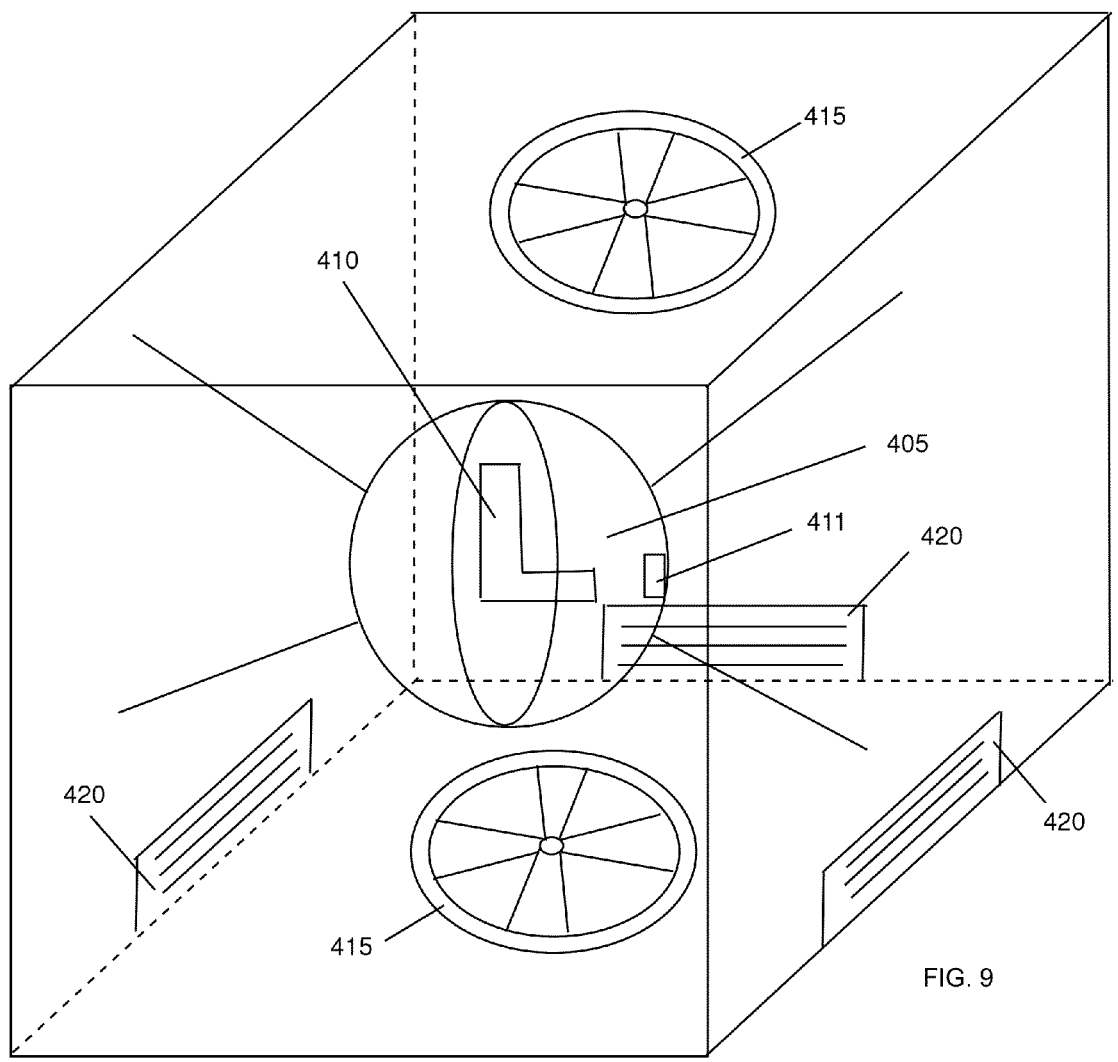
FIG. 9 illustrates a space cell for implementing the illustrated embodiment of the present invention.
Figure 9A:
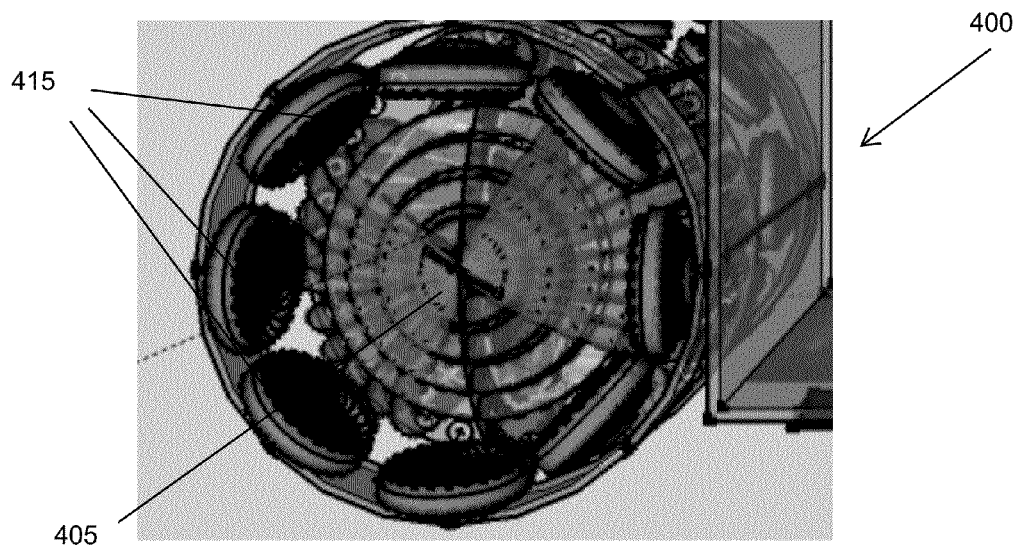
FIG. 9A is a top view of the space cell illustrated in FIG. 9.
Figure 9B:
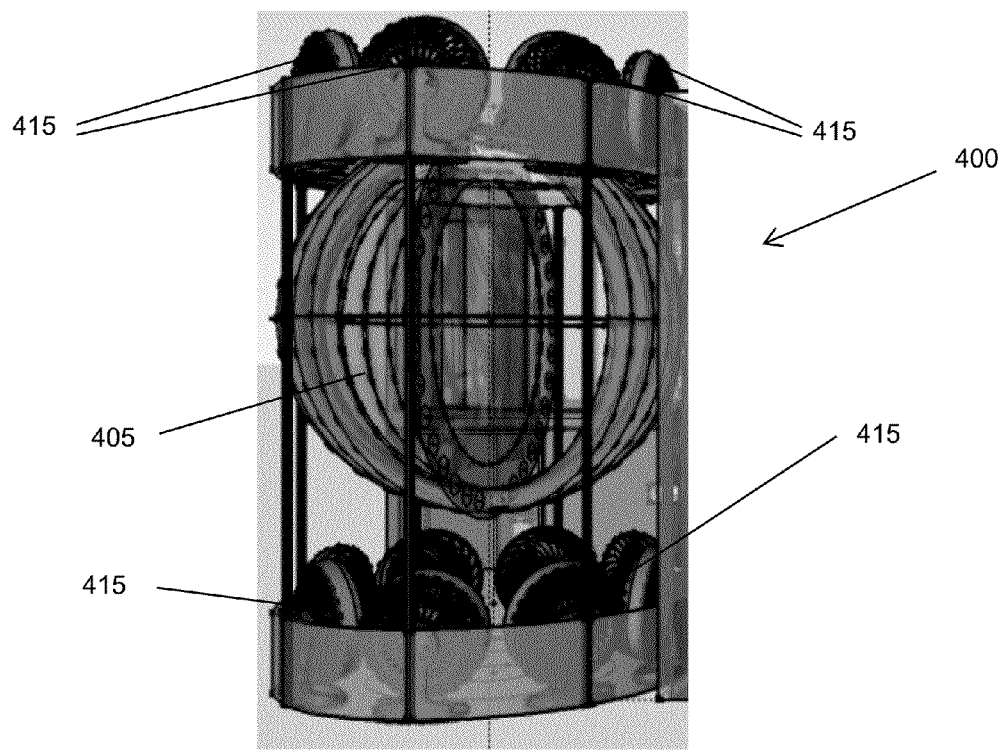
FIG. 9B is a front view of the space cell illustrated in FIG. 9.

Stratosphere or Dry Hot Desert Environment Illustrated in FIGS. 9, 9A, 9B

Element 1: Equipment

In one embodiment, the space cell is comprised of one or more of the following: (i) one gyroscope rotating in two dimensions, (ii) a vertical wind tunnel provided by a number of wind producing fans mounted to the floor, to the side of the gyroscope and the ceiling of the space cell, in one embodiment, the submission of the combined wind will vary between 60-100 miles per hour wind, and (iii) two electrical heaters mounted to the floor creating significant amount of heat produced by heat elements to raise the temperature of the vertical wind between 90° and 135° Fahrenheit, or as tolerated by the human subject.

Element 2: Environment

In the illustrated embodiment, the structure is enclosed in a fiberglass cylinder with the diameter of 10 feet and the vertical height of 15 feet of a structural steel column with horizontal steel pipes that support the fiberglass structure. The structure is fitted with an interior double door that opens and closes in a swivel pattern to maintain the operation of the equipment. Also provided is an entry door through the spa chamber 35 to provide access to the gyroscope from the spa room 35 of the Quadrex. The human subject is typically seated in a mounted seat in a central ring of the gyroscope. In one embodiment, the human subject typically has two options. Option A: remain seated and only rotate in the horizontal access or choose not to move at all just being exposed to the high heat drying winds. This condition will simulate a person caught in high heat wind storm in a desert environment. Option B: the human subject utilizes the full rotation of the gyroscope into the two axis's namely horizontal and vertical axis in a motion similar to an astronaut in space in a condition of weightlessness.

Element 3: Visual

In one embodiment, the visual element is produced by a video player connected to a viewing goggle that the human subject wear in front of his face as glasses, projecting a visual of a desert stormy environment or a space traveling environment. In another embodiment, cable or satellite television may be connected to the video player to further simulate any number of environments available as television programming.

FIG. 9 illustrates a space cell 400. Space cell 400 has a controlled space room temperature, regulated by heating elements 420 to maintain the controlled space room temperature between 95° and 135° Fahrenheit. In the illustrated embodiment, the space cell 400 has a plurality of fans 415 and a gyroscope 405. The gyroscope 405 is sized to contain a user and configured for imparting rotational movement to the user's body. FIG. 9A illustrates a top view of the space cell 400 of FIG. 9 and FIG. 9B illustrates a front view of the space cell 400 of FIG. 9, including placement of gyroscope 405 and a plurality of fans 415.

The gyroscope 405 shown in FIG. 9 has a seat for a user 410 with a footrest 411 and a first, inner ring mounted in an intermediate ring for rotation about a first axis. The second or intermediate ring is itself mounted in a third ring for rotation about a second axis extending perpendicular to the first axis. The outer ring, which has the greatest diameter of the three rings, is again mounted on a ground support for rotation about a third axis extending perpendicular to second axis. Ground support consists of a large-diameter ring made of a round tubular material and resting on the ground, and a pair of support risers disposed at opposite locations and carrying the ring assembly. At the location of the respective axes, the rings are carried by bearing assemblies for rotation relative to the respective adjacent ring, the bearing assemblies being offset with respect to one another by an angle of 90° for each consecutive ring. Depending on the height of a room, outer ring may also be mounted in the ceiling or a wall of a room.

Figure 10:
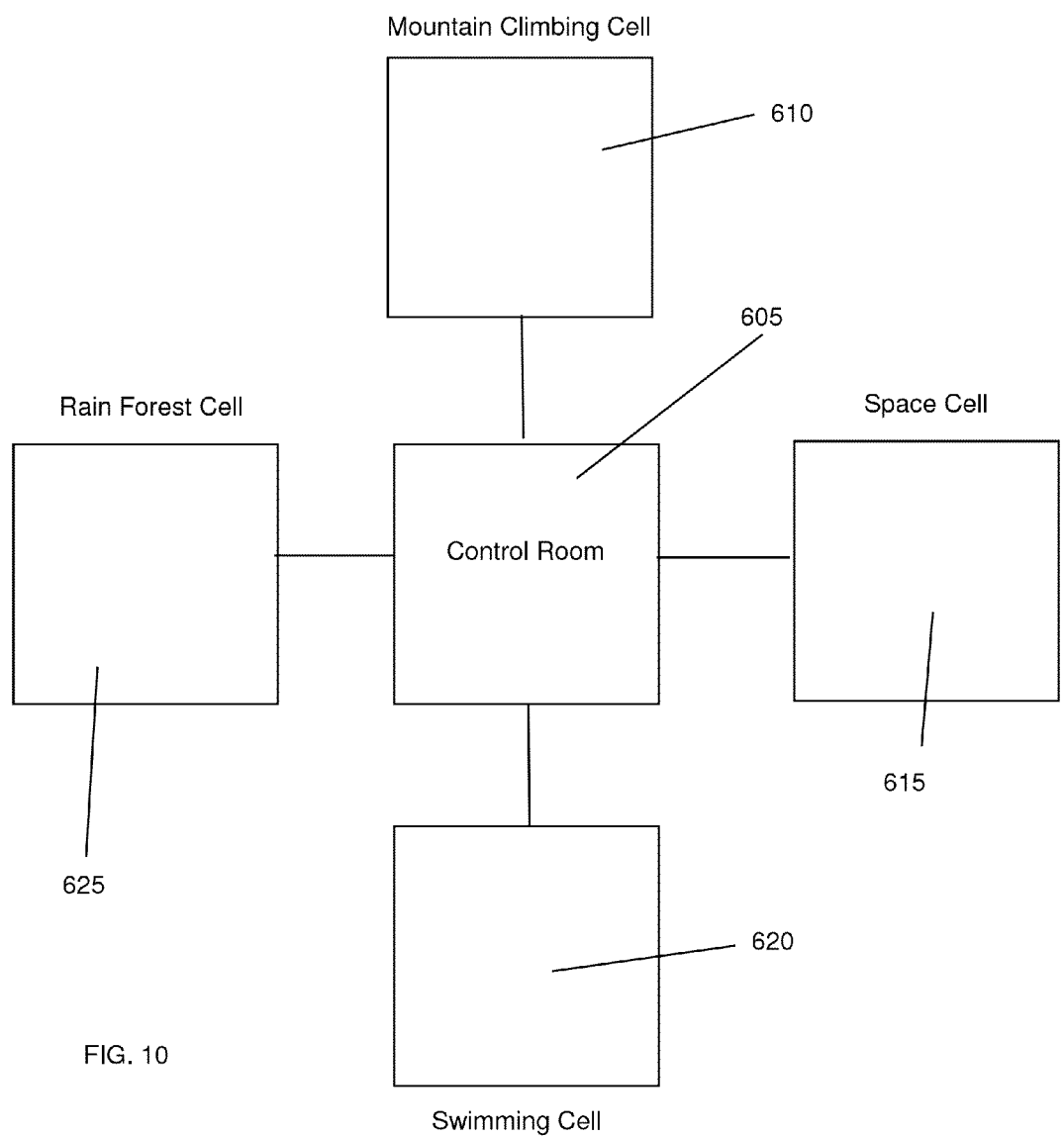
FIG. 10 illustrates a system for implementing the illustrated control room embodiment of the present invention.
Figure 15:
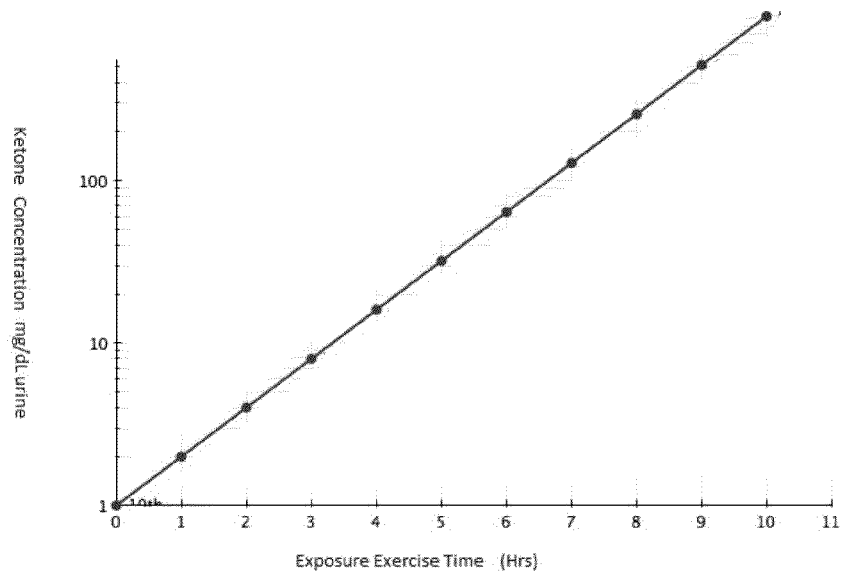

FIG. 10 illustrates a typical system 600 according to the present invention. In the illustrated embodiment, system 600 includes a control room 605 communicatively coupled to each of the exercise cells: mountain climbing cell 610, space cell 615, swimming cell 620 and rain forest cell 625. Control cell 605 comprises one or more displays coupled to cameras located in each of the exercise cells so that an operator may monitor the users exercising in each of the cells; cell controls for controlling the operation of each cell such as, for example, the wind and gyroscope operation in the space cell, the temperature in each of the exercise cells, the displayed images in the rain forest cell and mountain climbing cell and the duration and amount of rain in the rain forest cell; and user monitors to track health data for each user within the cell, such as, for example, heart rate and body temperature monitoring devices.

The Ketosis Inducing Process

The concept of a Ketosis state is best described as using the example of concept of a flying state. To achieve a flight, a machine is configured to produce enough thrust to lift the desired object to an upward anti-gravitational direction and to be able to cross a threshold speed to achieve this desired flying status. In a similar condition, the metabolic condition in the human subject body reaches a specific threshold for the long chain fatty acids in the adipose tissues to be enzymatically converted to the double carbon molecule (Ketone). When ketone molecules accumulate in the adipose tissue cells and blood stream to reach a certain threshold it will be expelled in urine. When the quantities of the Ketones expelled in urine reach a high enough level to test it with Ketone strips, this will be referred to as a Ketosis state. This ketosis state will continue so long as the Ketone concentration in the blood stream surpassed the kidney threshold of Ketones.

If the speed of the Ketosis state is slowed, such as by inactivity, then the Ketosis state may revert to a non-Ketosis state. This reversion is very similar to the process when a certain speed of the flying object is not maintained the gravitational forces will overcome the flying object (loss of thrust) and bring it down to the ground. In the similar condition, if the process of Ketosis is not maintained at a certain speed, it will be brought to a halt. This maintenance concept is what makes the exercise cell (the Ketosis Inducing Apparatus (KIA)/The Quadrex described herein) a unique machine, as it maintains the speed of the Ketosis process in a sustainable speed capable of maintaining a self-propagating status for maximum weight loss effect.

Step 1

Ketone Testing

As shown in FIG. 10B, Ketone testing is achieved with the use of ketone testing strips 650, 655 that change colors in a proportion to the amount of Ketone that is present in the human's urine sample. The step of ketone testing indicates if the subject has entered the state of ketosis, and therefore is ready to participate in the remaining steps of the method described herein.

Step 2

Pre-Ketosis Preparation

In accordance with one aspect of the process, there are many things that may be carried out prior to the subject's body entering the ketotic state. For example, in one aspect, colon cleansing of the subject may be achieved by use of medication for example, Amitza, (FDA colon approved stimulant), or osmodically neutral solutions for example GoLightly. In another example, the subject endures a 36 hour total fast from all foods and caloric fluids except for water and zero calorie fluids. In yet another example, the subject lives a CarboFree lifestyle for 1 week without medication; and, if capable, to abstain from starch and sugars carbohydrate foods to facilitate the transformation of the body to Ketosis state. In still another example, the subject lives a CarboFree lifestyle with medication; in this manner, for human incapable of abstaining from the carbohydrate elements in their food, an alternative use of medication for example, Phentermine (FDA approved appetite suppressant) when medically indicated.

For subjects who are not able to engage in rigorous activity, an alternative method is provided known herein as a Ketone Inducing Soaking Systems (KISS). The process of the KISS involves the use of alternating soaking in two different bath tubs 690 or wrapped in towels in covered chairs 695. The first bath tub consists of heated water as maximally tolerated by the human subject, usually between 104° and 115° Fahrenheit, and alternating in the second bath tub as maximally tolerated by the human subject usually 50° and 70° Fahrenheit.

Step 3

Ketosis Inducing Apparatus

The process that takes place in the Ketosis inducing four cell apparatus is described herein, namely the mountain cell, marine cell, tropical rain forest cell, and the space/desert storm cell. The rotation among the four cells, and the associated extreme environments associated therewith, simulates the maximum expenditure of energy output in the form of maximum thermal energy output and maximum kinetic energy output to achieve the maximum level of Ketosis state. In one embodiment, the human subject will undergo two possible cycle patterns, 4×15 minutes per cell.

In one embodiment, Cycle A, is to be repeated every hour up to eight hours. In another embodiment, Cycle B, the human subject will spend one hour in the mountain cell, followed by one hour in the marine cell, followed by one hour in the tropical rain forest/bike cell, followed by 30 minutes in the Space/Spa cell to achieve recovery. This rotation simulates a mini triathlon that takes about 3½ hours, to be followed by a repeat similar cycle for another mini triathlon for 3½ hours for a total of seven hours. The degree of difficulty will be customized according to the human's exercise and thermal challenge tolerability.

Mountain cell of FIGS. 6 and 6A: in a typical one hour cycle, the human subject will begin in the mountain cell of FIGS. 6 and 6A, using one of three available pieces of equipment. The subject may exercise on (i) a 16 foot, 35 degree incline conveyor belt to simulate hiking, (ii) a high incline treadmill at a 30 degree with a variable walking/running speeds, or (iii) on an elliptical equipment to simulate cross country skiing. All three pieces of equipment are placed in low temperature mountain cell simulating a mountain environment, with temperature varying between −20° to 40° Fahrenheit. Exercise takes place in front of a screen that is projecting a mountain environment, e.g. Mount Everest, Mount Hood, etc.

Marine or swimming cell of FIG. 7: the human subject will then transfer to the marine or swim cell of FIGS. 7 and 7A from the mountain cell of FIGS. 6 and 6A. The human subject descends into the water to exercise by swimming against a powerful swimming current created by the circulation of 800-gallon per minute submersed pumps. As an alternative to swimming, the subject may tread water, water jog, or water run, or whatever activity is comfortable so long as significant kinetic energy is being used. Typically, the water temperature varies between 50° and 70° Fahrenheit to effect shivering in the subject and through the thermal regulatory system.

Tropical rain forest cell of FIG. 8: The human subject then transfers to the tropical rain forest cell of FIGS. 8 and 8A from swimming cell of FIGS. 7 and 7A. The exercise typically utilizes a stationary bike or a training bike to provide the kinetic energy loss. Typically, the humidity in the cell is at or near 100% and the temperature varies between 90° and 135° Fahrenheit, with an average of 120°, but each will vary according to tolerability. The human subject will spend fifteen minutes in this environment; towards the end of this session a shower rain will be descending from shower heads mounted on the ceilings to simulate a rain forest.

Space/dry desert storm cell of FIG. 9: in one embodiment, the human subject then transfers to a recovery cell, such as a Spa cell. The subject utilizes the shower provided in this room as well as the massage table or exercise bench for a break/stretching. In another embodiment, the subject transfers to the space/desert storm cell, which contains the gyroscope mounted in the center of multiple fans and electric heaters. The subject may choose a stationary position in the gyroscope to dry and to experience the high wind speed vertical wind tunnel while watching a television monitor to display space or desert scenes. The human subject may also choose to be rotated in the gyroscope utilizing the automated motor to rotate motor/control the gyroscope in different directions for up to 5 minutes or up to maximum time tolerated by human subject.

In the illustrated embodiment, the human subject then transfers back to the mountain cell, and the cycle repeats itself up to eight times, or as tolerated by the human subject.

During the process, the subject is observed and checked with frequent Ketone testing to monitor the process to achieve the maximum Ketone output. The Ketone output will be measured in the scale from 0 output to 160 mg/dl, being 0 to signify no Ketosis detectable and 160 mg/dl being the maximum output of Ketone in urine.

The purpose of exposing the human subject to variable types of exercise namely hiking, running, walking, swimming, water walking, water jogging, cycling on stationary bike, or cycling on non-stationary bike, all these exercise forms are taking place in extreme cold or extreme hot conditions in the apparatus as described. The purpose of these variable exercise activities in the extreme cold/extreme hot environment is maximally stimulating the Ketosis process to take place; hence the purpose of this apparatus is Ketosis Inducing Apparatus (KIA).

Step 4

Post Ketosis Maintenance

Once the maximum status of Ketosis is achieved as described above, the human subject will leave the apparatus and facility with instructions on how to keep the Ketosis state alive which will further maximize his weight loss. These instructions will include the following follow-up and maintenance instructions.

In one embodiment, the subject is given a CarboFree Lifestyle Instructions. This is a maintenance diet that will be consumed by the human subject. The human subject will be allowed to consume a reasonable amount of food preferably under 2000 calories per day, but the main focus will be on the type of food consumed rather than the calorie intake. The human subject will be directed to abstain from the major high impacted carbohydrates, starch, and sugar intake, namely five subcategories of food: (i) Rice and rice products, (ii) Wheat and wheat products (bread, pasta, and cereal), (iii) Corn and corn syrup products (ice cream, variable snacks, sodas, etc.), (iv) Potatoes and potatoes products (basis of the fast food industry in the United Sates, in the form of french fries, baked potatoes, etc.), and (v) Sugars from various sources (e.g. cane sugar and other crystallized forms of sugar). All other carbohydrates foods that simulate these forms of food.

The subject is allowed to consume a diet based on protein, animal, and fish products and green vegetables. Dark chocolate will also be allowed. This type of diet/lifestyle will be easily maintained by the human subject. This diet will maintain the process of Ketosis in considerable speed unless interrupted by high impacted carbohydrate intake.

Non-Cellular Exercise (routine gym exercise): The human subject will be encourage to maintain their daily and weekly exercise program for about 50 minutes per day in a gym or in the comfort of his home with the purpose of maintaining the state of Ketosis in active form.

Repeat use of exercise cells and Ketosis Inducing Apparatus: This will be recommended to reignite the Ketosis state if the human subject has lost this condition due to large consumption of carbohydrates or due to complete lack of exercise activity. The human subject will be encouraged to return to the Ketone Inducing Apparatus exercise cells probably for a shorter amount of time (e.g. 2 or 4 hours) until he is able to regain the Ketosis state as described above.

A typical operation according to one embodiment of the method is described. First, a user enters the mountain climbing cell. The temperature in the mountain climbing cell is typically maintained between −20° and 40° Fahrenheit. The user proceeds to exercise within the simulated mountain environment, typically by walking up an inclined conveyor to simulate climbing a mountain within the simulated mountain environment. Next, the user leaves the mountain cell and enters the swimming cell. In the swimming cell, the user alternates between swimming in the simulated environment having a resistance swimming apparatus and a controlled water temperature between 50° and 90° Fahrenheit and standing on a platform pulling on a tension line that provides exercise resistance. The user leaves the swimming cell and enters the rain forest cell. In the rain forest cell, the user either rides a stationary bike or walks up an inclined conveyor in a controlled environment that has a controlled forest room temperature between 95° and 135° Fahrenheit and a humidity level at or near 100%. The user is intermittently doused with water to simulate rain in the simulated rain forest environment. The user then exits the rain forest cell and enters the space cell. The space cell has a gyroscope that operates in a windy environment having a controlled space room temperature is between 95° and 135° Fahrenheit. The gyroscope imparts rotational movement to the user's body in the simulated space environment. The user then repeats the cycle.

In one embodiment, the user spends approximately 15 minutes in each exercise cell. If the user enters and exercises in all four cells, the cell cycle for the illustrated embodiment equals approximately one-hour of exercise time. Under this example, a typical eight hour exercise session has eight cell cycles. However, one of ordinary skill in the art will realize that the session may be adjusted to fit a particular exercise program, such limiting which cells the user exercises within, limiting the duration of the session or cell cycles and/or limiting the number of cell cycles.

The illustrated Quadrex apparatus and use thereof has many uses and benefits for a wide-range of individuals, starting with individuals desiring significant weight loss. In addition, individuals who train for operations in severe conditions, such as military personnel or extreme athletes, may also benefit from a workout program with the Quadrex.

A new concept of exercise and weight loss that takes place in a unique environment, namely the exercise cells or the KIA, is illustrated and described above. The illustrated apparatus comprises four exercise cells to simulate four different exercise categories in extreme environments, namely walk/run/hike in a cold mountain environment, swim/water jog in a cold water marine environment, cycling in a hot, humid, rainy, tropical forest environment, and gravitational rotation in a hot dry air windy space or desert environment.

The purpose of this activity is to maximally stimulate the process of Ketosis (breakage of the human fat) to form smaller molecules of Ketones. The formed Ketones will then be eliminated from the human body passively via urination and exhalation and actively through intracellular burn. Hence, the process illustrated and described reduces the extra fat load and the extra stored fat load, and therefore reduces obesity. This process of Ketosis enhances the elimination of human fat and expedites the process of weight loss utilizing the exercise cells in the Ketosis inducing apparatus.

The relationship between exercise time exposure and the development of the Ketosis state is NOT a Linear relationship (e.g., as shown in FIG. 13). Instead, it is an S-Shape curve (similar to the multi-factorial biological processes for example oxygen saturation curve). As human subjects undergo Thermal and Kinetic Exercise Exposure in the Exercise Cells, the results manifest in a three phase S-Shaped Curve (e.g., as shown in FIG. 14).

Figure 16:
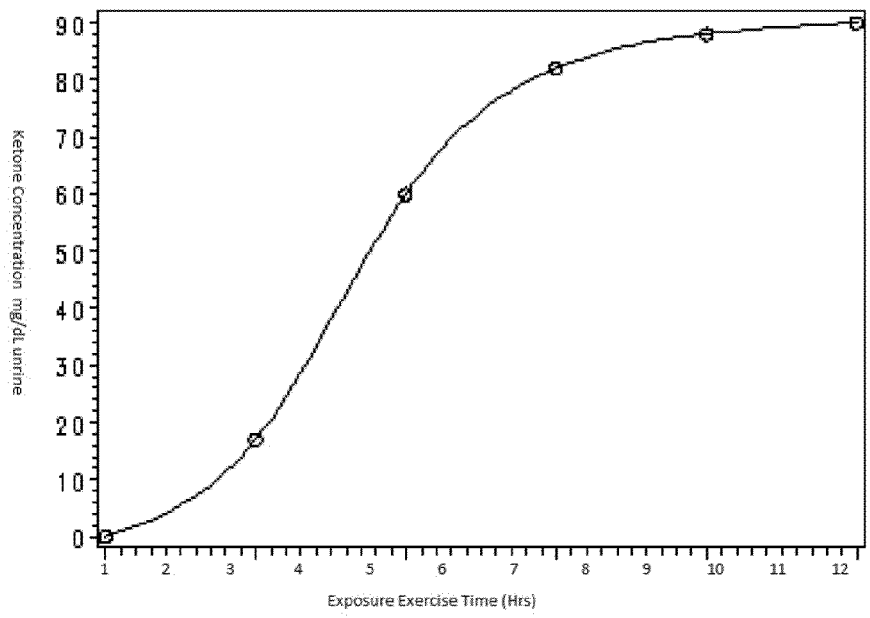

Phase I:

Muted Initial Phase, Where Ketone response is slowed down until a threshold point is reached (initial phase). In FIG. 16, the initial phase occurs at approximately 3.5 hours of exercise time.

Phase II:

Acceleration Phase. Where a small increments in time of Thermal and Kinetic exposure inside the exercise cells (after reaching the threshold) will lead to accelerated response in Ketone production (acceleration phase). In FIG. 16, the acceleration phase occurs from approximately 3.5 hours to 7.5 hours of exercise time, Phase III:

The Last Plateau Phase where the prolonged exposure to Thermal and Kinetic Exercise Exposure in the Exercise Cells will produce minimal increments of Ketone production in the human subject. In FIG. 16, the plateau phase occurs at approximately 7.5 hours of exercise time and beyond.

The Ketosis Inducing Apparatus (KIA) captures the acceleration phase of the Ketosis process in a human subject, thus providing a unique contribution to the field of weight loss. The KIA provides the unique combination of Thermal and Kinetic Energy exposure needed to cross the threshold between Non-Ketotic and Ketotic state (i.e., between the initial phase and the accelerated phase of Ketosis). Significantly, the KIA provides a method and apparatus that can predictably induce, accelerate and maintain the Ketosis process in human subjects.

The reduction of the human fat and decrease of obesity will enhance the human health status and reduce many of the associated complications of obesity, such as diabetes and heart disease, and improves the human subject's mortality and morbidity that is accompanying these conditions.

Tri-Ex/Tri Athlon Training Indoor Machine

Another utilization of the exercise cells will be Tri-Athlon Training Indoor Machine (Tri-A-Trim), The TRI-EX, also known as ½ Tri-Athlon Gym (½ t. gym). FIGS. 11-12 illustrate an alternate embodiment of the exercise cells, referred to herein for purposes of illustration as the TRI-EX 700, shown from the front perspective view in FIG. 12 is comprised of three exercise cells, namely: (i) Swimming Cell 720, (ii) Cycling Cell 715, and (iii) Running Cell 725. In the illustrated embodiment shown from the top in FIG. 11, the construct of the three cells of the TRI-EX 700 is very similar to the description of mountain cell 25, marine cell 20, and tropical rain forest cell 15 as previously described. The utility of the TRI-EX 700 provides training session for athletes contemplating training for a triathlon competitions with variable environmental elements introduced as required. Triathlon training varies from the previous description in that athletes will not undergo the prep stage and therefore it will not be required to reach the ketosis state to achieve their training objective.

The cycle for the Tri-Athlon Athletes Training consist of three phases to simulate the three phases of a Tri-Athlon.

1. Swimming Phase

Typically, the swimming phase takes place in swimming cell 720 for about 1-3 hours of constant swimming in variable current speeds to simulate the natural condition that the athlete would experience in the expected triathlon.

2. Cycling Phase

Typically, the cycling phase takes place in cycling cell for about 1-3 hours, or as prolonged a period of time as needed by the athlete to experience the same condition similar to the expected course of the triathlon.

3. Running Phase

The running phase will take place in running cell 725 in similar course as expected in the triathlon course.

In the illustrated embodiment of FIGS. 11-12, the equipment, environment and visual experience of the TRI-EX 700 is focused on training of triathletes preparing for upcoming triathlon competitions and structured to simulate the expected course features and climate requirements of a typical triathlon as closely as possible. The value of the exercise cells will provide three cells simulating swimming, cycling, and the running features of the triathlon in an indoor environment. This will be replicated to reflect the specific features of this triathlon for example temperature of the water during the swimming segment of the course, the temperature and elevation of the cycling course, and the temperature and elevation of the running course.

In this context, attention is focused on the athletic performance of the triathlete rather than the weight loss aspect of the human subject. Accordingly, no specific attention is devoted to either Ketosis or fasting and preparation prior to athletic performance. Rather, attention is focused on the endurance of the athlete and the acquiring of the experience of the specific features of the triathlon course.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

I claim:

1. An apparatus for cellular exercising, comprising:
    at least two exercise cells simulating a natural environment, said exercise cell chosen from a group consisting of a mountain climbing cell/running cell, a rain forest cell/biking cell, a marine environment cell/swimming cell and a space/desert cell,
    said mountain climbing cell comprises a controlled mountain room temperature, said mountain climbing cell further comprising a climbing cell exercise apparatus and a projector, said projector configured to show images on a screen in view of a person utilizing said climbing cell exercise apparatus,
    said marine environment cell comprises water at a controlled temperature and speed, said marine environment cell having a resistance swimming apparatus enabling a person to swim in place,
    said rain forest cell comprises a controlled rain forest room temperature, said rain forest cell further comprising a plurality of shower heads, a projector and a cycling exercise apparatus, said shower heads configured for introducing water to said rain forest cell to simulate rain, said projector configured to show images on a screen in view of a person utilizing said cycling exercise apparatus, and
    said space cell comprises a controlled space room temperature, said space cell having a plurality fans, a gyroscope and a projector, said gyroscope sized to contain a user and configured for imparting rotational movement to the user's body, said projector configured to show images pertaining to space and desert environment.

2. The apparatus of claim 1, wherein said exercise apparatus comprises an incline with a conveyor to simulate climbing on a mountain path.

3. The apparatus of claim 1, wherein said controlled mountain room temperature is between −20° and 40° Fahrenheit.

4. The apparatus of claim 1, wherein said resistance swimming apparatus comprises a countercurrent swimming machine having a water tank and an adjustable stream of water set in motion by means of a mechanical device.

5. The apparatus of claim 4, wherein said controlled water temperature is between 50° and 90° degrees Fahrenheit.

6. The apparatus of claim 1, wherein said marine environment cell further comprises a platform and a tension line to provide exercise resistance.

7. The apparatus of claim 1, wherein said exercise apparatus comprises a stationary exercise bike or a mountain exercise bike on accessory training equipment.

8. The apparatus of claim 1, wherein said controlled forest room temperature is between 95° and 135° Fahrenheit.

9. The apparatus of claim 1, wherein said gyroscope further comprises:
    a first, inner frame element serving as a carrier for an occupant and mounted in a second, larger frame element for rotation about a first axis, said second frame element being itself mounted in a third frame element for rotation about a second axis extending transversely of the first axis, wherein the third frame element is mounted for rotation about a third axis extending perpendicular to the second axis, so that mounting permits a person occupying the inner frame element to assume any angular position in space solely by displacement of his weight, the three frame elements are formed as nested rings made of round tubular sections; and
    a motor drive assembly for rotating the inner frame element about a first axis relative to the larger second frame element.

10. The apparatus of claim 1, wherein said controlled space room temperature is between 95° and 135° Fahrenheit.

11. An exercise method comprising:
    placing a user in a state of ketosis for weight loss;
    providing a mountain climbing cell having a controlled mountain room temperature, wherein said mountain climbing cell further comprising an exercise apparatus and a projector, said projector configured to show images on a screen or video glasses in view of a person utilizing said exercise apparatus;
    providing a marine environment cell having water at a controlled temperature and speed, wherein said marine environment cell has a resistance swimming apparatus controlling said speed to enable a person to swim in place;
    providing a rain forest cycling cell having a controlled forest room temperature, wherein said rain forest cell further comprises a plurality of shower heads, a projector and an exercise cycling apparatus, said shower heads configured for introducing water to said rain forest cell to simulate rain, said projector configured to show images on a screen in view of a person utilizing said exercise apparatus;

providing a space cell having a controlled space room temperature, wherein said space cell has a plurality fans and a gyroscope, said gyroscope sized to contain a user and configured for imparting rotational movement to the user's body; and having said user exercise in one or more cells, wherein said user spends a predetermined time within each cell.

12. The method of claim 11, wherein a user exercises in each of the four cells, and wherein a user spends a predetermined time of 15 minutes in each cell for a 1-hour cycle.

13. The method of claim 12, wherein said user performs a succession of eight 1-hour cycles per exercise session.

14. The method of claim 11, wherein said placing of said user in a state of ketosis further comprises carbohydrate flushing and colon cleansing.

15. The method of claim 14, wherein said carbohydrate flushing further comprises 36 hours of medically supported fasting.

16. The method of claim 11, further comprising measuring the level of ketosis in the user by ketone testing strips that change colors in a proportion to the amount of Ketone that is present in the human's urine sample.

17. An exercise system comprising:
a mountain climbing cell/running cell having a controlled mountain room temperature, wherein said controlled mountain room temperature is between −20° and 40° Fahrenheit, said mountain climbing cell further comprising a climbing cell exercise apparatus and a projector, said projector configured to show images on a screen in view of a person utilizing said exercise apparatus, said exercise apparatus having an incline with a conveyor to simulate climbing on a mountain path;

a marine environment cell/swimming cell having water at a controlled temperature and speed, wherein said controlled water temperature is between 50° and 90° Fahrenheit, said marine environment cell having a resistance swimming apparatus enabling a person to swim or water jog in place;

a rain forest cell/cycling cell having a controlled forest room temperature, wherein said rain forest cell further comprises a plurality of shower heads, a projector and an exercise cycling apparatus, said shower heads configured for introducing water to said rain forest cell to simulate rain, said projector configured to show images on a screen in view of a person utilizing said exercise cycling apparatus;

a space cell/desert cell having a controlled space room temperature, wherein said controlled space room temperature is between 95° and 135° Fahrenheit, said space cell having a plurality fans, a gyroscope and a projector, said gyroscope sized to contain a user and configured for imparting rotational movement to said user's body.

18. The apparatus of claim 17, further comprising a control room communicatively coupled to said mountain climbing cell/running cell, swimming cell/marine cell, rain forest cell/cycling cell and space cell/desert cell, said control room comprising displays to monitor the activities in each of the cells, said control room configured to control the environment and operation of each cell.

* * * * *